US012371642B2

(12) United States Patent
Smets et al.

(10) Patent No.: US 12,371,642 B2
(45) **Date of Patent: *Jul. 29, 2025**

(54) BENEFIT AGENT CONTAINING DELIVERY PARTICLE

(71) Applicant: The Procter & Gamble Company, Cincinnati, OH (US)

(72) Inventors: Johan Smets, Lubbeek (BE); Corey James Kenneally, Mason, OH (US); Ariel Lebron, Cincinnati, OH (US); Pascale Claire Annick Vansteenwinckel, Weerde (BE); Robert Stanley Bobnock, Menasha, WI (US); Peggy Dorothy Sands, Appleton, WI (US); Todd Arlin Schwantes, Lena, WI (US); Chad Alexander Hladilek, Appleton, WI (US)

(73) Assignee: The Procter & Gamble Company, Cincinnati, OH (US)

( * ) Notice: Subject to any disclaimer, the term of this patent is extended or adjusted under 35 U.S.C. 154(b) by 146 days.

This patent is subject to a terminal disclaimer.

(21) Appl. No.: 18/327,383

(22) Filed: Jun. 1, 2023

(65) Prior Publication Data

US 2023/0313084 A1 Oct. 5, 2023

Related U.S. Application Data

(63) Continuation of application No. 16/565,525, filed on Sep. 10, 2019, now Pat. No. 11,708,546, and a continuation of application No. PCT/US2017/022614, filed on Mar. 16, 2017.

(51) Int. Cl.

| | |
|---|---|
| ***C11D 17/00*** | (2006.01) |
| ***C11D 3/00*** | (2006.01) |
| ***C11D 3/22*** | (2006.01) |
| ***C11D 3/37*** | (2006.01) |
| ***C11D 3/382*** | (2006.01) |
| ***C11D 3/50*** | (2006.01) |
| ***C11D 17/04*** | (2006.01) |

(52) U.S. Cl.

CPC .......... *C11D 17/0039* (2013.01); *C11D 3/001* (2013.01); *C11D 3/505* (2013.01); *C11D 2111/12* (2024.01)

(58) Field of Classification Search

None

See application file for complete search history.

(56) References Cited

U.S. PATENT DOCUMENTS

| | | | | |
|---|---|---|---|---|
| 9,186,642 | B2 | 11/2015 | Dihora | |
| 9,579,676 | B1 | 2/2017 | Burrowes | |
| 9,890,351 | B2 | 2/2018 | Smets | |
| 9,993,793 | B2 | 6/2018 | Dihora | |
| 10,920,177 | B2 | 2/2021 | Smets et al. | |
| 11,708,546 | B2 | 7/2023 | Smets et al. | |
| 11,713,437 | B2 * | 8/2023 | Smets .................. | C11D 3/2093 510/418 |
| 2010/0286018 | A1 | 11/2010 | Hentze | |
| 2011/0268802 | A1 | 11/2011 | Dihora | |
| 2012/0276210 | A1 | 11/2012 | Dihora | |
| 2013/0039962 | A1 | 2/2013 | Smets | |
| 2013/0203644 | A1 | 8/2013 | Lant | |
| 2013/0302392 | A1 | 11/2013 | Mistry | |
| 2014/0342964 | A1 | 11/2014 | Jackson et al. | |
| 2015/0000048 | A1 | 1/2015 | Miracle | |
| 2016/0024434 | A1 | 1/2016 | Sivik | |
| 2017/0002293 | A1 | 1/2017 | Dihora | |
| 2017/0002301 | A1 | 1/2017 | Dihora | |
| 2017/0002302 | A1 | 1/2017 | Dihora | |
| 2018/0265818 | A1 | 9/2018 | Smets | |
| 2020/0002653 | A1 | 1/2020 | Smets | |
| 2020/0002654 | A1 | 1/2020 | Smets | |

FOREIGN PATENT DOCUMENTS

| | | | |
|---|---|---|---|
| CN | 1257533 | A | 6/2000 |
| CN | 1965068 | A | 5/2007 |
| CN | 101541939 | A | 9/2009 |
| CN | 102858940 | A | 1/2013 |
| CN | 102892492 | A | 1/2013 |
| CN | 103458858 | A | 12/2013 |
| CN | 103747771 | A | 4/2014 |
| EP | 2687590 | A2 | 1/2014 |
| JP | 2000218154 | A | 8/2000 |
| WO | 2009150017 | A1 | 12/2009 |
| WO | 2010079468 | A2 | 7/2010 |
| WO | 2012138696 | A2 | 10/2012 |
| WO | 2015041791 | A1 | 3/2015 |
| WO | 2016014733 | A1 | 1/2016 |
| WO | 2016061440 | A1 | 4/2016 |
| WO | 2017004343 | A1 | 1/2017 |

OTHER PUBLICATIONS

PCT Search Report and written opinion for PCT/US2017/022614 dated Nov. 16, 2017; 15 pages.
All Office Actions U.S. Appl. No. 16/565,523, filed Sep. 10, 2019.
All Office Actions; U.S. Appl. No. 16/565,525, filed Sep. 10, 2019.
Celvol Polyvinyl Alcohol; A Versatile High-Performance Polymer, Internet Citation, Jan. 1, 2007, pp. 1-16, XP002632184, retrieved from the Internet: URL: http://www.celanese.com/celvol_polyvinyl_alcohol.pdf [retrieved on Apr. 8, 2011] the whole document.
Ichemco, Selvol 540, dated Mar. 14, 2013, 1 page.
Sekisui: Selvol Polyvinyl Alcohol—A Versatile High-Performance Polymer; Mar. 30, 2015, pp. 1-9, XP055422301, retrieved from the Internet: URL: http://www. sekisui-sc.com/wp content/uploads/SelvolPVOH_Brochure_EN.pdf [retrieved on Nov. 7, 2017] the whole document.

* cited by examiner

*Primary Examiner* — Lorna M Douyon
(74) *Attorney, Agent, or Firm* — Carolyn S. Powell; Andrew J. Mueller

(57) ABSTRACT

Benefit agent containing delivery particles that can be supplied as slurries, compositions comprising such particles, and processes for making and using such particles and compositions.

18 Claims, No Drawings

BENEFIT AGENT CONTAINING DELIVERY PARTICLE

FIELD OF INVENTION

The present application relates to benefit agent containing delivery particles comprising a core and a shell encapsulating said core, compositions comprising such particles, and processes for making and using such particles and compositions.

JOINT RESEARCH AGREEMENT

The inventions described and claimed herein were made pursuant to a Joint Research Agreement between The Procter & Gamble Company and Encapsys, LLC (Appleton, WI, USA).

BACKGROUND OF THE INVENTION

Benefit agents, such as perfumes, silicones, waxes, flavors, vitamins and fabric softening agents, are expensive and/or generally less effective when employed at high levels in consumer products, for example, personal care compositions, cleaning compositions, and fabric care compositions. As a result, there is a desire to maximize the effectiveness of such benefit agents. One method of achieving such objective is to improve the delivery efficiencies of such benefit agents. Unfortunately, it is difficult to improve the delivery efficiencies of benefit agents as such agents may be lost due to the agents' physical or chemical characteristics, or such agents may be incompatible with other compositional components or the situs that is treated. In an effort to improve such delivery efficiency, benefit agents have been encapsulated.

It is desired that benefit agent containing delivery particles having a shell that comprises a polyacrylate, provide perfume benefits across all consumer touch points. For example, it is desired that such particles provide a perfume benefit to fabrics that are treated with such particles when the fabrics are still wet from such treatment and after such fabrics have been dried. Unfortunately, such particles leak benefit agent over time, possibly via diffusion. Thus, the fabric odor is reduced. If such leakage is minimized, for example, by increasing the particle's shell strength, the wet and/or dry fabric odor may again be reduced. This problem is particularly pronounced in fabric treatment products, such as liquid fabric enhancers, liquid laundry detergents, unit dose laundry detergents and granule/powdered laundry detergents that comprise such particles. Thus, what is needed are particles that exhibit decreased benefit agent leakage, yet which provide the desired odor profile—in particular an enhanced prerub benefit and a post rub benefit to wet and dry fabrics.

Here, Applicants recognized that the source of the problem giving rise to shell strength vs. benefit agent release dilemma in the benefit agent delivery system was a multicomponent problem. This multicomponent problem is rooted in the colloid type, the monomeric building block for the capsule wall, and the benefit agent solvent system because colloids and capsule shell polymers both form an integrated delivery system and the polymerization process is influenced by the benefit agent solvent system. The level, type and the molecular weight of the colloid, for example polyvinyl alcohol, used in combination with capsule shell polymers that formed during the particle making process can influence the effectiveness of the delivery system. This is especially true when such delivery agent polymer shell is also partly built from monomers with numerous crosslinking sites/moieties such as acrylate moieties. In general, the molecular weight and crosslinking of the non-colloid part of the delivery system is difficult to control. Surprisingly, Applicants recognized that such control can be obtained if not only the shell materials, but also the colloid type, and benefit agent solvent system that is encapsulated are judiciously selected. Also the benefit agent solvent system plays a role in the molecular weight obtained and the crosslinking in the polymers obtained in the non-colloid part of the delivery system. While not being bound by theory, Applicants therefore believe that the type, level and the molecular weight of the selected colloid combined with the resulting shell polymer of the delivery systems and the particle size of the delivery system impacts the odor profile (intensity or character) that the delivery system can provide.

While such a judicious selection will provide the desired benefit, benefit agent containing delivery particles are normally supplied as slurries and the use of polyvinyl alcohol as a colloid can decrease the stability of slurries that contains the particles. Applicants discovered that the source of this problem was that some of the polyvinyl alcohol used to manufacture the particles is found as free polyvinyl alcohol in the slurry. In short, this free polyvinyl alcohol is not incorporated in the shell that encapsulates the benefit agent. Such free polyvinyl alcohol results in a depletion flocculation of the benefit agent containing delivery particles that destabilizes the slurry. Such depletion flocculation is exacerbated by the presence of salt. In order to achieve an acceptable level of stability, the level of free polyvinyl alcohol can be reduced by properly selecting the level of polyvinyl alcohol used in making the benefit agent containing delivery particles, the type of polyvinyl alcohol can be judiciously selected, more efficient benefit agent containing delivery particles making processes can be used and/or the slurry can be refined to remove free polyvinyl alcohol. Preferably, the salt level is also minimized. As a result, benefit agent containing delivery particles that can be supplied as slurries and that exhibit decreased benefit agent leakage, yet which provide the desired odor profile—in particular an enhanced prerub benefit and a post rub benefit to wet and dry fabrics can be made and used. Processes for making and using such benefit agent containing delivery particles as well as compositions comprising same are provided herein.

SUMMARY OF THE INVENTION

The present application relates to benefit agent containing delivery particles comprising a core and a shell encapsulating said core, compositions comprising such particles, and processes for making and using such particles and compositions.

DETAILED DESCRIPTION OF THE INVENTION

Definitions

As used herein "consumer product" means baby care, beauty care, fabric & home care, family care, feminine care, health care, snack and/or beverage products or devices intended to be used or consumed in the form in which it is sold, and not intended for subsequent commercial manufacture or modification. Such products include but are not limited to fine fragrances (e.g. perfumes, colognes eau de toilettes, after-shave lotions, pre-shave, face waters, tonics, and other fragrance-containing compositions for application directly to the skin), diapers, bibs, wipes; products for and/or methods relating to treating hair (human, dog, and/or cat), including, bleaching, coloring, dyeing, conditioning, shampooing, styling; deodorants and antiperspirants; personal cleansing; cosmetics; skin care including application of creams, lotions, and other topically applied products for consumer use; and shaving products, products for and/or methods relating to treating fabrics, hard surfaces and any other surfaces in the area of fabric and home care, including: air care, car care, dishwashing, fabric conditioning (including softening), laundry detergency, laundry and rinse additive and/or care, hard surface cleaning and/or treatment, and other cleaning for consumer or institutional use; products and/or methods relating to bath tissue, facial tissue, paper handkerchiefs, and/or paper towels; tampons, feminine napkins; products and/or methods relating to oral care including toothpastes, tooth gels, tooth rinses, denture adhesives, tooth whitening; over-the-counter health care including cough and cold remedies, pain relievers, RX pharmaceuticals, pet health and nutrition, and water purification; processed food products intended primarily for consumption between customary meals or as a meal accompaniment (non-limiting examples include potato chips, tortilla chips, popcorn, pretzels, corn chips, cereal bars, vegetable chips or crisps, snack mixes, party mixes, multigrain chips, snack crackers, cheese snacks, pork rinds, corn snacks, pellet snacks, extruded snacks and bagel chips); and coffee.

As used herein, the term “cleaning composition” includes, unless otherwise indicated, granular or powder-form all-purpose or “heavy-duty” washing agents, especially cleaning detergents; liquid, gel or paste-form all-purpose washing agents, especially the so-called heavy-duty liquid types; liquid fine-fabric detergents; hand dishwashing agents or light duty dishwashing agents, especially those of the high-foaming type; machine dishwashing agents, including the various pouches, tablet, granular, liquid and rinse-aid types for household and institutional use; liquid cleaning and disinfecting agents, including antibacterial hand-wash types, cleaning bars, mouthwashes, denture cleaners, dentifrice, car or carpet shampoos, bathroom cleaners; hair shampoos and hair-rinses; shower gels and foam baths and metal cleaners; as well as cleaning auxiliaries such as bleach additives and “stain-stick” or pre-treat types, substrate-laden products such as dryer added sheets, dry and wetted wipes and pads, nonwoven substrates, and sponges; as well as sprays and mists.

As used herein, the term “fabric care composition” includes, unless otherwise indicated, fabric softening compositions, fabric enhancing compositions, fabric freshening compositions and combinations thereof. The form of such compositions includes liquids, gels, beads, powders, flakes, and granules.

As used herein, the phrase “benefit agent containing delivery particle” encompasses microcapsules including perfume microcapsules.

As used herein, the terms “particle”, “benefit agent containing delivery particle”, “encapsulated benefit agent”, “capsule” and “microcapsule” are synonymous.

As used herein, reference to the term “(meth)acrylate” or “(meth)acrylic” is to be understood as referring to both the acrylate and the methacrylate versions of the specified monomer, oligomer and/or prepolymer, (for example “allyl (meth)acrylate” indicates that both allyl methacrylate and allyl acrylate are possible, similarly reference to alkyl esters of (meth)acrylic acid indicates that both alkyl esters of acrylic acid and alkyl esters of methacrylic acid are possible, similarly poly(meth)acrylate indicates that both polyacrylate and polymethacrylate are possible). Poly(meth)acrylate materials are intended to encompass a broad spectrum of polymeric materials including, for example, polyester poly (meth)acrylates, urethane and polyurethane poly(meth)acrylates (especially those prepared by the reaction of an hydroxyalkyl (meth)acrylate with a polyisocyanate or a urethane polyisocyanate), methylcyanoacrylate, ethylcyanoacrylate, diethyleneglycol di(meth)acrylate, trimethylolpropane tri(meth)acrylate, ethylene glycol di(meth)acrylate, allyl(meth)acrylate, glycidyl (meth)acrylate, (meth)acrylate functional silicones, di-, tri- and tetraethylene glycol di(meth)acrylate, dipropylene glycol di(meth)acrylate, polyethylene glycol di(meth)acrylate, di(pentamethylene glycol)di (meth)acrylate, ethylene di(meth)acrylate, neopentyl glycol di(meth)acrylate, trimethylol propane tri(meth)acrylate, ethoxylated bisphenol A di(meth)acrylates, bisphenol A di(meth)acrylates, digylcerol di(meth)acrylate, tetraethylene glycol dichloroacrylate, 1,3-butanediol di(meth)acrylate, neopentyl di(meth)acrylate, trimethylolpropane tri(meth) acrylate, polyethylene glycol di(meth)acrylate and dipropylene glycol di(meth)acrylate and various multifunctional (meth)acrylates. Monofunctional acrylates, i.e., those containing only one acrylate group, may also be advantageously used. Typical monoacrylates include 2-ethylhexyl (meth)acrylate, 2-hydroxyethyl (meth)acrylate, cyanoethyl (meth)acrylate, 2-hydroxypropyl (meth)acrylate, p-dimethylaminoethyl (meth)acrylate, lauryl (meth)acrylate, cyclohexyl (meth)acrylate, tetrahydrofurfuryl (meth)acrylate, chlorobenzyl (meth)acrylate, aminoalkyl(meth)acrylate, various alkyl(meth)acrylates and glycidyl (meth)acrylate. Of course mixtures of (meth)acrylates or their derivatives as well as combinations of one or more (meth)acrylate monomers, oligomers and/or prepolymers or their derivatives with other copolymerizable monomers, including acrylonitriles and methacrylonitriles may be used as well.

For purposes of this application, castor oil, soybean oil, brominated vegetable oil, propan-2-yl tetradecanoate and mixtures thereof are not considered a perfume raw material when calculating perfume compositions/formulations. Thus, the amount of Propan-2-yl tetradecanoate present is not used to make such calculations.

As used herein, the articles including “a” and “an” when used in a claim, are understood to mean one or more of what is claimed or described.

As used herein, the terms “include”, “includes” and “including” are meant to be non-limiting.

The test methods disclosed in the Test Methods Section of the present application should be used to determine the respective values of the parameters of Applicants' inventions.

Unless otherwise noted, all component or composition levels are in reference to the active portion of that component or composition, and are exclusive of impurities, for example, residual solvents or by-products, which may be present in commercially available sources of such components or compositions.

All percentages and ratios are calculated by weight unless otherwise indicated. All percentages and ratios are calculated based on the total composition unless otherwise indicated.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Consumer Products

Consumer products are disclosed in this section of this application. The reference to preceding paragraphs found in this section of this application only applies to paragraphs found in this section of this application. Paragraphs are denoted by an upper case letter in round brackets, for example (A).

(A) A composition comprising a consumer product adjunct material and benefit agent containing delivery particles, preferably said composition comprises, based on total consumer product weight from about 0.0003% to about 11%, more preferably from about 0.1% to about 2%, most preferably from about 0.3% to about 1% of said benefit agent containing delivery particles, said benefit agent containing delivery particles comprising a core and a shell encapsulating said core, said benefit agent containing delivery particles comprising:

a) based on total benefit agent containing delivery particle core weight from about 0.1% to about 1.1% polyvinyl alcohol, preferably 0.3% to 1% polyvinyl alcohol, more preferably 0.6% to 0.9% polyvinyl alcohol; said polyvinyl alcohol based on total encapsulated benefit agent particle core weight preferably having at least one the following properties, more preferably at least two of the following properties, more preferably at least three of the following properties, most preferably all of the following properties:

(i) a hydrolysis degree from about 55% to about 99%, preferably from about 75% to about 95%, more preferably from about 85% to about 90%, most preferably from about 87% to about 89%;

(ii) a viscosity of from about 40 mPa·s to about 120 mPa·s, preferably from about 40 mPa·s to about 90 mPa·s, more preferably from about 45 mPa·s to about 72 mPa·s, more preferably from about 45 mPa·s to about 60 mPa·s, most preferably 45 mPa·s to 55 mPa·s in 4% water solution at 20° C.;

(iii) a degree of polymerization of from about 1,500 to about 2,500, preferably from about 1,600 to about 2,200, more preferably from about 1,600 to about 1,900, most preferably from about 1,600 to about 1,800;

(iv) number average molecular weight of from about 65,000 Da to about 110,000 Da, preferably from about 70,000 Da to about 101,000 Da, more preferably from about 70,000 Da to about 90,000 Da, most preferably from about 70,000 Da to about 80,000 Da;

b) said benefit agent containing delivery particles preferably having a volume weighted mean particle size from about 0.5 microns to about 100 microns, preferably from about 1 micron to about 60 microns, preferably said benefit agent containing delivery particles' shell comprising, said polyvinyl alcohol and one or more polyacrylate polymers, said core comprising, based on total core weight, greater than 10%, preferably from greater than 20% to about 80%, from greater than 20% to about 70%, more preferably from greater than 20% to about 60%, more preferably from about 25% to about 60%, most preferably from about 25% to about 50% of a partitioning modifier that comprises a material selected from the group consisting of propan-2-yl tetradecanoate, vegetable oil, modified vegetable oil and mixtures thereof, preferably said modified vegetable oil is esterified and/or brominated, preferably said vegetable oil comprises castor oil and/or soy bean oil;

said composition being a consumer product.

(B) A composition according to Paragraph (A) wherein, said partitioning modifier comprises propan-2-yl tetradecanoate is disclosed.

(C) A composition according to any of Paragraphs (A) through (B) wherein, said shell comprises a polyacrylate, preferably said shell comprises from about 50% to about 100%, more preferably from about 70% to about 100%, most preferably from about 80% to about 100% of said polyacrylate polymer, preferably said polyacrylate comprises a polyacrylate cross linked polymer, is disclosed.

(D) A composition according to any of Paragraphs (A) through (C) wherein, said shell comprises a polymer derived from a material that comprises one or more multifunctional acrylate moieties; preferably said multifunctional acrylate moiety is selected from group consisting of tri-functional acrylate, tetra-functional acrylate, penta-functional acrylate, hexa-functional acrylate, hepta-functional acrylate and mixtures thereof; and optionally a polyacrylate that comprises a moiety selected from the group consisting of an amine acrylate moiety, methacrylate moiety, a carboxylic acid acrylate moiety, carboxylic acid methacrylate moiety and combinations thereof, is disclosed.

(E) A composition according to any of Paragraphs (A) through (D) wherein, said shell comprises a polymer derived from a material that comprises one or more multifunctional acrylate and/or methacrylate moieties, preferably the ratio of material that comprises one or more multifunctional acrylate moieties to material that comprises one or more methacrylate moieties is 999:1 to about 6:4, more preferably from about 99:1 to about 8:1, most preferably from about 99:1 to about 8.5:1; preferably said multifunctional acrylate moiety is selected from group consisting of tri-functional acrylate, tetra-functional acrylate, penta-functional acrylate, hexa-functional acrylate, hepta-functional acrylate and mixtures thereof; and optionally a polyacrylate that comprises a moiety selected from the group consisting of an amine acrylate moiety, methacrylate moiety, a carboxylic acid acrylate moiety, carboxylic acid methacrylate moiety and combinations thereof, is disclosed.

(F) A composition according to any of Paragraphs (A) through (E) wherein, said benefit agent containing delivery particles having a volume weighted mean particle size from about 5 microns to about 45 microns more preferably from about 8 microns to about 25 microns, or alternatively a volume weighted mean particle size from about 25 microns to about 60 microns, more preferably from about 25 microns to about 60 microns, said composition comprising, based on total composition weight, from about 0.1% to about 35%, preferably from about 1% to about 35%, more preferably from about 2% to about 25%, more preferably from about 3% to about 20%, more preferably from about 5% to about 15%, most preferably from about 8% to about 12% of a fabric softener active or from about 3% to about 12%, preferably from about 4% to about 10%, more preferably from about 5% to about 8% of a fabric softener active, preferably said fabric softener active is selected from the group consisting of quaternary ammonium compounds, amines, fatty esters, sucrose esters, silicones, dispersible polyolefins, clays, polysaccharides, fatty acids, softening oils, polymer latexes and mixtures thereof, more preferably said fabric softener active is selected from the group consisting of bis-(2-hydroxypropyl)-dimethylammonium methylsulphate fatty acid ester, 1,2-di(acyloxy)-3-trimethylammoniopropane chloride, N, N-bis(stearoyl-oxy-ethyl)-N,N-dimethyl ammonium chloride, N,N-bis(tallowoyl-oxy-ethyl) N,N-dimethyl ammonium chloride, N,N-bis(stearoyl-oxy-ethyl)N-(2 hydroxyethyl)-N-methyl ammonium methylsulfate, N,N-bis-(stearoyl-2-hydroxypropyl)-N,N-dimethylammonium methylsulphate, N,N-bis-(tallowoyl-2-hydroxypropyl)-N,N-dimethylammonium methylsulphate, N,N-bis-(palmitoyl-2-hydroxypropyl)-N,N-dimethylammonium methylsulphate, N,N-bis-(stearoyl-2-hydroxypropyl)-N,N-dimethylammonium chloride, 1,2 di(stearoyl-oxy) 3 trimethyl ammoniumpropane chloride, dicanoladimethylammonium chloride, di(hard)tallowdimethylammonium chloride dicanoladimethylammonium methylsulfate, 1-methyl-1-stearoylamidoethyl-2-stearoylimidazolinium methylsulfate, 1-tallowylamidoethyl-2-tallowylimidazoline, Dipalmethyl Hydroxyethylammonium Methosulfate and mixtures thereof, and mixtures thereof, most preferably said fabric softener active is selected from the group consisting of N, N-bis(stearoyl-oxy-ethyl) N,N-dimethyl ammonium chloride; N,N-bis(tallowoyl-oxy-ethyl) N,N-dimethyl ammonium chloride; N,N-bis(stearoyl-oxy-ethyl)N-(2 hydroxyethyl)N-methyl ammonium methylsulfate; 1,2 di(stearoyl-oxy) 3 trimethyl ammoniumpropane chloride; N,N-bis-(stearoyl-2-hydroxypropyl)-N,N-dimethylammonium methylsulphate, N,N-bis-(tallowoyl-2-hydroxypropyl)-N,N-dimethylammonium methylsulphate, N,N-bis-(palmitoyl-2-hydroxypropyl)-N,N-dimethylammonium methylsulphate, N,N-bis-(stearoyl-2-hydroxypropyl)-N,N-dimethylammonium chloride, and mixtures thereof, is disclosed.

(G) A composition according to of Paragraphs (A) through (F), said composition comprising, based on total composition weight, from about 5% to about 95%, preferably from about 10% to about 95%, more preferably from about 20% to about 95%, more preferably from about 30% to about 80%, most preferably from about 50% to about 70% water and from about 0.1% to about 25%, preferably from about 0.5% to about 20% of a surfactant, preferably said surfactant is selected from the group consisting of nonionic or anionic surfactants and mixtures thereof, is disclosed.

(H) A composition according any of Paragraphs (A) through (G) wherein, said composition comprises, based on total composition weight, from about 5% to about 20%, from about 8% to about 15%, from about 9% to about 13% water said composition being encased in a film, preferably said film comprising polyvinylalcohol, is disclosed.

(I) A composition according to any of Paragraphs (A) through (G), said composition comprising a liquid and/or gel and a film, said film encasing said liquid and/or gel, optionally said liquid or gel comprising a suspended solid, is disclosed.

(J) A composition according to any of Paragraphs (A) through (G) wherein, said benefit agent containing delivery particles have a volume weighted mean particles size from about 2 microns to about 40 microns, preferably from about 8 microns to about 25 microns, said composition comprising based on total composition weight, from about 5% to about 95% free water and from about 0.5% to about 25% of a builder, is disclosed.

(K) A composition according to any of Paragraphs (A) through (J), comprising, based on total composition weight, a material selected from the group consisting of a hueing dye, a structurant, an additional perfume delivery system and mixtures thereof; preferably a) said structurant comprises a material selected from the group consisting of polysaccharides, preferably said polysaccharides are selected from the group consisting of modified celluloses, chitosan, plant cellulose, bacterial cellulose, coated bacterial cellulose, preferably said bacterial cellulose comprises xanthan gum; castor oil, hydrogenated castor oil, modified proteins, inorganic salts, quaternized polymeric materials, imidazoles; nonionic polymers having a pKa less than 6.0, polyurethanes, non-polymeric crystalline hydroxyl-functional materials, polymeric structuring agents, diamido gellants, a homopolymer of Formula (Ia) below:

(Ia)

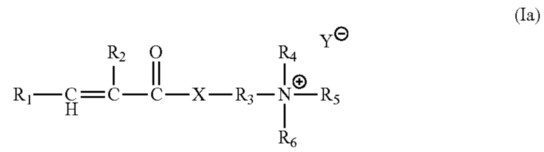

wherein:

$R_1$ is chosen from hydrogen or methyl;

$R_2$ is chosen hydrogen, or $C_1$-$C_4$ alkyl;

$R_3$ is chosen $C_1$-$C_4$ alkylene;

$R_4$, $R_5$, and $R_6$ are each independently chosen from hydrogen, or $C_1$-$C_4$ alkyl;

X is chosen from —O—, or —NH—, preferably —O—; and

Y is chosen from Cl, Br, I, hydrogensulfate or methosulfate;

and mixtures thereof;

b) said hueing dye is selected from the group consisting of small molecule dyes, polymeric dyes, dye-clay conjugates, and organic and inorganic pigments, preferably said hueing dye comprises a chromophore selected from one or more of the following: acridine, anthraquinone, azine, azo, azulene, benzodifurane and benzodifuranone, carotenoid, coumarin, cyanine, diazahemicyanine, diphenylmethane, formazan, hemicyanine, indigoids, methane, naphthalimides, naphthoquinone, nitro and nitroso, oxazine, phthalocyanine, pyrazoles, stilbene, styryl, triarylmethane, triphenylmethane, xanthenes and mixtures thereof; and c) said additional perfume delivery comprises a material selected from the group consisting of a second benefit agent containing delivery particle, a polymer assisted delivery system; a molecule-assisted delivery system; a fiber-assisted delivery system; a cyclodextrin delivery system; a starch encapsulated accord; and/or an inorganic carrier delivery system.

(L) A composition according to any of Paragraphs (A) through (K) wherein, said benefit agent containing delivery particles are produced by a radical polymerization process that comprises the step of combining, based on total radical polymerization process acrylate monomer reactants, from about 50% to about 100% of a hexa-functional urethane acrylate and/or a penta-functional urethane acrylate, from about 0% to about 25%, preferably from about 0.01% to about 25% of a methacrylate that comprises an amino moiety and from about 0% to about 25%, preferably from about 0.01% to about 25% of an acrylate comprising a carboxyl moiety, with the proviso that the sum of the hexa-functional urethane acrylate and/or penta-functional urethane acrylate, methacrylate that comprises an amino moiety and acrylate comprising a carboxyl moiety is 100%, preferably said methacrylate that comprises an amino moiety comprises tertiarybutylaminoethyl methacrylate and said acrylate comprising a carboxyl moiety comprises beta carboxyethyl acrylate, is disclosed.

(M) A composition according to any of Paragraphs (A) through (L), comprising a deposition aid, preferably said deposition aid coats the outer surface of said delivery particles' shell, preferably said deposition aid comprises a material selected from the group consisting of poly(meth) acrylate, poly(ethylene-maleic anhydride), polyamine, wax, polyvinylpyrrolidone, polyvinylpyrrolidone co-polymers, polyvinylpyrrolidone-ethyl acrylate, polyvinylpyrrolidone-vinyl acrylate, polyvinylpyrrolidone methylacrylate, polyvinylpyrrolidone/vinyl acetate, polyvinyl acetal, polyvinyl butyral, polysiloxane, poly(propylene maleic anhydride), maleic anhydride derivatives, co-polymers of maleic anhydride derivatives, polyvinyl alcohol, styrene-butadiene latex, gelatin, gum Arabic, carboxymethyl cellulose, carboxymethyl hydroxyethyl cellulose, hydroxyethyl cellulose, other modified celluloses, sodium alginate, chitosan, casein, pectin, modified starch, polyvinyl acetal, polyvinyl butyral, polyvinyl methyl ether/maleic anhydride, polyvinyl pyrrolidone and its co polymers, poly(vinyl pyrrolidone/methacrylamidopropyl trimethyl ammonium chloride), polyvinylpyrrolidone/vinyl acetate, polyvinyl pyrrolidone/dimethylaminoethyl methacrylate, polyvinyl amines, polyvinyl formamides, polyallyl amines and copolymers of polyvinyl amines, polyvinyl formamides, polyallyl amines and mixtures thereof, more preferably said deposition aid comprises a material selected from the group consisting of poly(meth)acrylates, poly(ethylene-maleic anhydride), polyamine, polyvinylpyrrolidone, polyvinylpyrrolidone-ethyl acrylate, polyvinylpyrrolidone-vinyl acrylate, polyvinylpyrrolidone methylacrylate, polyvinylpyrrolidone/vinyl acetate, polyvinyl acetal, polyvinyl butyral, polysiloxane, poly(propylene maleic anhydride), maleic anhydride derivatives, co-polymers of maleic anhydride derivatives, polyvinyl alcohol, chitosan, carboxymethyl cellulose, carboxymethyl hydroxyethyl cellulose, hydroxyethyl cellulose, polyvinyl methyl ether/maleic anhydride, poly(vinyl pyrrolidone/methacrylamidopropyl trimethyl ammonium chloride), polyvinylpyrrolidone/vinyl acetate, polyvinyl pyrrolidone/dimethylaminoethyl methacrylate, polyvinyl amines, polyvinyl formamides, polyallyl amines and copolymers of polyvinyl amines, polyvinyl formamides, polyallyl amines and mixtures thereof, is disclosed.

Process of Making Consumer Products

The present application discloses a unique composition, composition-by-process, and process of making compositions comprising benefit agent containing delivery particles comprising a core and a shell encapsulating said core. The reference to preceding paragraphs found in this section of this application only applies to paragraphs found in this section and the preceding section of this application. New paragraphs in this section are denoted by an upper case letter and a number in round brackets, for example (A1).

(A1) A process of making a consumer product, preferably a consumer product according to Paragraphs (A) through (M), comprising combining a consumer product adjunct ingredient and the benefit agent containing delivery particles made by a process comprising:

emulsifying the combination of a) and b) to form an emulsion, wherein a) is a first composition formed by combining a first oil and a second oil, said first oil comprising a core comprising a perfume, an initiator, and a partitioning modifier, preferably said partitioning modifier comprises a material selected from the group consisting of vegetable oil, modified vegetable oil, propan-2-yl tetradecanoate and mixtures thereof, preferably said modified vegetable oil is esterified and/or brominated, preferably said vegetable oil comprises castor oil and/or soy bean oil; preferably said partitioning modifier comprises propan-2-yl tetradecanoate;

said second oil comprising (i) an oil soluble aminoalkylacrylate and/or methacrylate monomer;

(ii) a hydroxy alkyl acrylate monomer and/or oligomer;

(iii) a material selected from the group consisting of a multifunctional acrylate monomer, multifunctional methacrylate monomer, multifunctional methacrylate oligomer, multifunctional acrylate oligomer and mixtures thereof;

(iv) a perfume; and wherein b) is a second composition comprising a continuous phase, a pH adjuster, an emulsifier, preferably an anionic emulsifier, preferably said emulsifier comprises polyvinyl alcohol, and optionally an initiator; and, heating the emulsion in one or more heating steps to form a shell encapsulating the core, thereby forming benefit agent containing delivery particles comprising the shell encapsulating the core, said benefit agent containing delivery particles being dispersed in a continuous phase, is disclosed.

The compositions disclosed herein can be made by combining the slurry disclosed herein with the desired consumer product adjuncts materials. The slurry may be combined with such one or more consumer product adjuncts materials when they are in one or more forms, including a neat slurry form, neat particle form and spray dried particle form. The particles may be combined with such consumer product adjuncts materials by methods that include mixing and/or spraying.

The cleaning and/or treatment compositions of the present invention can be formulated into any suitable form and prepared by any process chosen by the formulator, non-limiting examples of which are described in U.S. Pat. No. 5,879,584 which is incorporated herein by reference.

Suitable equipment for use in the processes disclosed herein may include continuous stirred tank reactors, homogenizers, turbine agitators, recirculating pumps, paddle mixers, plough shear mixers, ribbon blenders, vertical axis granulators and drum mixers, both in batch and, where available, in continuous process configurations, spray dryers, and extruders. Such equipment can be obtained from Lodige GmbH (Paderborn, Germany), Littleford Day, Inc. (Florence, Kentucky, U.S.A.), Forberg A S (Larvik, Norway), Glatt Ingenieurtechnik GmbH (Weimar, Germany), Niro (Soeborg, Denmark), Hosokawa Bepex Corp. (Minneapolis, Minnesota, U.S.A.), Arde Barinco (New Jersey, U.S.A.).

Perfume Raw Materials

Perfume raw materials that are useful as core materials are disclosed below.

TABLE 1

| Useful Perfume Raw Materials | | |
|---|---|---|
| Item | Common Name | IUPAC Name |
| 1 | Methyl 2-methyl butyrate | methyl 2-methylbutanoate |
| 2 | Isopropyl 2-methyl butyrate | propan-2-yl 2-methylbutanoate |
| 3 | Ethyl-2 Methyl Butyrate | ethyl 2-methylbutanoate |
| 4 | Ethyl-2 Methyl Pentanoate | ethyl 2-methylpentanoate |
| 5 | Ethyl heptanoate | ethyl heptanoate |
| 6 | Ethyl octanoate | Ethyl octanoate |
| 7 | isobutyl hexanoate | 2-methylpropyl hexanoate |
| 8 | Amyl butyrate | pentyl butanoate |
| 9 | Amyl heptanoate | Pentyl heptanoate |
| 10 | Isoamyl isobutyrate | 3-methylbutyl 2-methylpropanoate |
| 11 | Hexyl acetate | hexyl acetate |
| 12 | hexyl butyrate | hexyl butanoate |
| 13 | hexyl isobutyrate | hexyl 2-methylpropanoate |
| 14 | hexyl isovalerate | hexyl 3-methylbutanoate |
| 15 | hexyl propionate | hexyl propanoate |
| 16 | Ethyl 2-cyclohexyl propanoate | ethyl 2-cyclohexylpropanoate |
| 17 | Ethyl 3,5,5-trimethyl hexanoate | ethyl 3,5,5-trimethylhexanoate |
| 18 | glyceryl 5-hydroxydecanoate | 2,3-dihydroxypropyl 5-hydroxydecanoate |
| 19 | Prenyl acetate | 3-methyl 2-butenyl acetate |
| 20 | 3-methyl 2-butenyl acetate | 3-methyl 2-butenyl acetate |
| 21 | methyl 3-nonenoate | methyl non-3-enoate |
| 22 | Ethyl (E)-dec-4-enoate | Ethyl (E)-dec-4-enoate |
| 23 | Ethyl (E)-oct-2-enoate | Ethyl (E)-oct-2-enoate |
| 24 | Ethyl 2,4-decadienoate | ethyl (2E,4Z)-deca-2,4-dienoate |
| 25 | Ethyl 3-octenoate | ethyl (E)-oct-3-enoate |
| 26 | Citronellyl acetate | 3,7-dimethyloct-6-enyl acetate |
| 27 | Ethyl trans-2-decenoate | ethyl (E)-dec-2-enoate |
| 28 | 2-hexen-1-yl isovalerate | [(E)-hex-2-enyl] acetate |
| 29 | 2-hexen-1-yl propionate | [(E)-hex-2-enyl] propanoate |
| 30 | 2-hexen-1-yl valerate | [(E)-hex-2-enyl] pentanoate |
| 31 | 3-hexen-1-yl (E)-2-hexenoate | [(Z)-hex-3-enyl] (E)-hex-2-enoate |
| 32 | 3-Hexen-1-yl 2-methyl butyrate | [(Z)-hex-3-enyl] 2-methylbutanoate |
| 33 | 3-hexen-1-yl acetate | [(Z)-hex-3-enyl] acetate |
| 34 | 3-hexen-1-yl benzoate | [(Z)-hex-3-enyl] benzoate |
| 35 | 3-hexen-1-yl formate | [(Z)-hex-3-enyl] formate |
| 36 | 3-hexen-1-yl tiglate | [(Z)-hex-3-enyl] (Z)-2-methylbut-2-enoate |
| 37 | 2-methyl butyl 2-methyl butyrate | 2-methylbutyl 2-methylbutanoate |
| 38 | Butyl isovalerate | butyl 3-methylbutanoate |
| 39 | Geranyl acetate | [(2E)-3,7-dimethylocta-2,6-dienyl] acetate |
| 40 | Geranyl butyrate | [(2E)-3,7-dimethylocta-2,6-dienyl] butanoate |
| 41 | Geranyl isovalerate | [(3E)-3,7-dimethylocta-3,6-dienyl] 3-methylbutanoate |
| 42 | Geranyl propionate | [(2E)-3,7-dimethylocta-2,6-dienyl] propanoate |
| 43 | Allyl cyclohexane acetate | prop-2-enyl 2-cyclohexylacetate |
| 44 | Allyl Cyclohexyl Propionate | prop-2-enyl 3-cyclohexylpropanoate |
| 45 | allyl cyclohexyl valerate | prop-2-enyl 5-cyclohexylpentanoate |
| 46 | benzyl octanoate | benzyl octanoate |
| 47 | cocolactone | 6-pentyl-5,6-dihydropyran-2-one |
| 48 | coconut decanone | 8-methyl-1-oxaspiro(4.5)decan-2-one |
| 49 | gamma undecalactone | 5-heptyloxolan-2-one |
| 50 | gamma-decalactone | 5-hexyloxolan-2-one |
| 51 | gamma-dodecalactone | 5-octyloxolan-2-one |
| 52 | jasmin lactone | 6-[(E)-pent-2-enyl]oxan-2-one |
| 53 | Jasmolactone | 5-[(Z)-hex-3-enyl]oxolan-2-one |
| 54 | Nonalactone | 6-butyloxan-2-one |
| 55 | 6-acetoxydihydrotheaspirane | [2a,5a(S*)]-2,6,10,10-tetramethyl-1-oxaspiro[4.5]decan-6-yl acetate |
| 56 | Phenoxyethyl isobutyrate | 2-(phenoxy)ethyl 2-methylpropanoate |
| 57 | Pivacyclene | |
| 58 | Verdox | (2-tert-butylcyclohexyl) acetate |
| 59 | cyclobutanate | 3a,4,5,6,7,7a-hexahydro-4,7-methano-1g-inden-5(or 6)-yl butyrate |
| 60 | Dimethyl Anthranilate | methyl 2-methylaminobenzoate |
| 61 | Methyl Antranilate | methyl 2-aminobenzoate |
| 62 | Octyl Aldehyde | Octanal |
| 63 | Nonanal | Nonanal |
| 64 | Decyl aldehyde | Decanal |
| 65 | Lauric Aldehyde | Dodecanal |
| 66 | Methyl Nonyl Acetaldehyde | 2-methyl undecanal |
| 67 | Methyl Octyl Acetaldehyde | 2-methyl decanal |
| 68 | 2,4-Hexadienal | (2E,4E)-hexa-2,4-dienal |
| 69 | Intreleven Aldehyde | undec-10-enal |
| 70 | Decen-1-al | (E)-dec-2-enal |

TABLE 1-continued

| Useful Perfume Raw Materials | | |
|---|---|---|
| Item | Common Name | IUPAC Name |
| 71 | Nonen-1-al | (E)-2-nonen-1-al |
| 72 | Adoxal | 2,6,10-trimethylundec-9-enal |
| 73 | Geraldehyde | (4Z)-5,9-dimethyldeca-4,8-dienal |
| 74 | Iso cyclo citral | 2,4,6-trimethylcyclohex-3-ene-1-carbaldehyde |
| 75 | d-limonene mainly | 1-methyl-4-prop-1-en-2-yl-cyclohexene |
| 76 | Ligustral | 2,4-dimethylcyclohex-3-ene-1-carbaldehyde |
| 77 | Myrac aldehyde | 4-(4-methylpent-3-enyl)cyclohex-3-ene-1-carbaldehyde |
| 78 | Tridecenal | tridec-2-enal |
| 79 | Triplal | 2,4-dimethyl-3-cyclohexene-1-carboxaldehyde |
| 80 | Vertoliff | 1,2-dimethylcyclohex-3-ene-1-carbaldehyde |
| 81 | Cyclal C | 2,4-dimethylcyclohex-3-ene-1-carbaldehyde |
| 82 | Anisic aldehyde | 4-methoxybenzaldehyde |
| 83 | Helional | 3-(1,3-benzodioxol-5-yl)-2-methylpropanal |
| 84 | Heliotropin | 1,3-benzodioxole-5-carbaldehyde |
| 85 | Neocaspirene | |
| 86 | Beta Naphthol Ethyl Ether | 2-ethoxynaphtalene |
| 87 | Beta Naphthol Methyl Ether | 2-methoxynaphtalene |
| 88 | hyacinth ether | 2-cyclohexyloxyethylbenzene |
| 89 | 2-heptyl cyclopentanone (fleuramone) | 2-heptylcyclopentan-1-one |
| 90 | menthone-8-thioacetate | O-[2-[(1S)-4-methyl-2-oxocyclohexyl]propan-2-yl] ethanethioate |
| 91 | Nectaryl | 2-[2-(4-methyl-1-cyclohex-3-enyl)propyl]cyclopentan-1-one |
| 92 | Phenyl Naphthyl Ketone | naphthalen-2-yl-phenylmethanone |
| 93 | decen-1-yl cyclopentanone | 2-[(2E)-3,7-dimethylocta-2,6-dienyl] cyclopentan-1-one |
| 94 | fruity cyclopentanone (veloutone) | 2,2,5-trimethyl-5-pentylcyclopentan-1-one |
| 95 | 4-methoxy-2-methyl butane thiol (blackcurrant mercaptan) | 4-methoxy-2-methylbutane-2-thiol |
| 96 | Grapefruit Mercaptan | 2-(4-methyl-1-cyclohex-3-enyl)propane-2-thiol |
| 97 | Buccoxime | N-(1,5-dimethyl-8-bicyclo[3.2.1]octanylidene)hydroxylamine |
| 98 | Labienoxime | 2,4,4,7-Tetramethyl-6,8-nonadiene-3-one oxime |
| 99 | Undecavertol | (E)-4-methyldec-3-en-5-ol |
| 100 | Decanal diethyl acetal | 1,1-diethoxydecane |
| 101 | Diethyl maleate | diethyl but-2-enedioate |
| 102 | Ethyl Acetoacetate | ethyl 3-oxobutanoate |
| 103 | frutonile | 2-Methyldecanenitrile |
| 104 | Methyl dioxolan | ethyl 2-(2-methyl-1,3-dioxolan-2-yl)acetate |
| 105 | Cetalox | 3a,6,6,9a-tetramethyl-2,4,5,5a,7,8,9,9b-octahydro-1H-benzo[e][1]benzofuran |
| 106 | Cyclopentol | |
| 107 | Delta-damascone | (E)-1-(2,6,6-trimethyl-1-cyclohex-3-enyl)but-2-en-1-one |
| 108 | Eucalyptol | 1,3,3-trimethyl-2-oxabicyclo[2,2,2]octane |
| 109 | Flor acetate | |
| 110 | Ionone gamma methyl | (E)-3-methyl-4-(2,6,6-trimethyl-1-cyclohex-2-enyl)but-3-en-2-one |
| 111 | Laevo trisandol | |
| 112 | Linalool | 3,7-dimethylocta-1,6-dien-3-ol |
| 113 | Violiff | [(4Z)-1-cyclooct-4-enyl] methyl carbonate |
| 114 | Cymal | 3-(4-propan-2-ylphenyl)butanal |
| 115 | Bourgeonal | 3-(4-tert-butylphenyl)propanal |

Consumer Product Adjunct Ingredients

The disclosed compositions may include additional adjunct ingredients that include: bleach activators, surfactants, builders, chelating agents, dye transfer inhibiting agents, dispersants, enzymes, and enzyme stabilizers, catalytic metal complexes, polymeric dispersing agents, clay and soil removal/anti-redeposition agents, suds suppressors, dyes, additional perfumes and perfume delivery systems, structure elasticizing agents, fabric softeners, carriers, hydrotropes, processing aids, structurants, anti-agglomeration agents, coatings, formaldehyde scavengers and/or pigments. Other variants of Applicants' compositions do not contain one or more of the following adjuncts materials: bleach activators, surfactants, builders, chelating agents, dye transfer inhibiting agents, dispersants, enzymes, and enzyme stabilizers, catalytic metal complexes, polymeric dispersing agents, clay and soil removal/anti-redeposition agents, suds suppressors, dyes, additional perfumes and perfume delivery systems, structure elasticizing agents, fabric softeners, carriers, hydrotropes, processing aids, structurants, anti-agglomeration agents, coatings, formaldehyde scavengers, malodor reduction materials and/or pigments. The precise nature of these additional components, and levels of incorporation thereof, will depend on the physical form of the composition and the nature of the operation for which it is to be used. However, when one or more adjuncts are present, such one or more adjuncts may be present as detailed below. The following is a non-limiting list of suitable additional adjuncts.

Deposition Aid—The fabric treatment composition may comprise from about 0.01% to about 10%, from about 0.05 to about 5%, or from about 0.15 to about 3% of a deposition aid. The deposition aid may be a cationic or amphoteric polymer. The deposition aid may be a cationic polymer. Cationic polymers in general and their method of manufacture are known in the literature. The cationic polymer may have a cationic charge density of from about 0.005 to about 23 meq/g, from about 0.01 to about 12 meq/g, or from about 0.1 to about 7 meq/g, at the pH of the composition. For amine-containing polymers, wherein the charge density depends on the pH of the composition, charge density is measured at the intended use pH of the product. Such pH will generally range from about 2 to about 11, more generally from about 2.5 to about 9.5. Charge density is calculated by dividing the number of net charges per repeating unit by the molecular weight of the repeating unit. The positive charges may be located on the backbone of the polymers and/or the side chains of polymers.

The deposition aid may comprise a cationic acrylic based polymer. The deposition aid may comprise a cationic polyacrylamide. The deposition aid may comprise a polymer comprising polyacrylamide and polymethacrylamidopropyl trimethylammonium cation. The deposition aid may comprise poly(acrylamide-N-dimethyl aminoethyl acrylate) and its quaternized derivatives.

The deposition aid may be selected from the group consisting of cationic or amphoteric polysaccharides. The deposition aid may be selected from the group consisting of cationic and amphoteric cellulose ethers, cationic or amphoteric galactomannan, cationic guar gum, cationic or amphoteric starch, and combinations thereof.

Another group of suitable cationic polymers may include alkylamine-epichlorohydrin polymers which are reaction products of amines and oligoamines with epichlorohydrin. Another group of suitable synthetic cationic polymers may include polyamidoamine-epichlorohydrin (PAE) resins of polyalkylenepolyamine with polycarboxylic acid. The most common PAE resins are the condensation products of diethylenetriamine with adipic acid followed by a subsequent reaction with epichlorohydrin.

The weight-average molecular weight of the polymer may be from about 500 Daltons to about 5,000,000 Daltons, or from about 1,000 Daltons to about 2,000,000 Daltons, or from about 2,500 Daltons to about 1,500,000 Daltons, as determined by size exclusion chromatography relative to polyethylene oxide standards with RI detection. The weight-average molecular weight of the cationic polymer may be from about 500 Daltons to about 37,500 Daltons.

Surfactants: Surfactants utilized can be of the anionic, nonionic, zwitterionic, ampholytic or cationic type or can comprise compatible mixtures of these types. Anionic and nonionic surfactants are typically employed if the fabric care product is a laundry detergent. On the other hand, cationic surfactants are typically employed if the fabric care product is a fabric softener. In addition to the anionic surfactant, the fabric care compositions of the present invention may further contain a nonionic surfactant. The compositions of the present invention can contain up to about 30%, alternatively from about 0.01% to about 20%, more alternatively from about 0.1% to about 10%, by weight of the composition, of a nonionic surfactant. The nonionic surfactant may comprise an ethoxylated nonionic surfactant. Suitable for use herein are the ethoxylated alcohols and ethoxylated alkyl phenols of the formula $R(OC_2H_4)n\ OH$, wherein R is selected from the group consisting of aliphatic hydrocarbon radicals containing from about 8 to about 20 carbon atoms and alkyl phenyl radicals in which the alkyl groups contain from about 8 to about 12 carbon atoms, and the average value of n is from about 5 to about 15.

Suitable nonionic surfactants are those of the formula $R1(OC_2H_4)_nOH$, wherein R1 is a $C_{10}$-$C_{16}$ alkyl group or a $C_8$-$C_{12}$ alkyl phenyl group, and n is from 3 to about 80. Particularly useful materials are condensation products of $C_9$-$C_{15}$ alcohols with from about 5 to about 20 moles of ethylene oxide per mole of alcohol.

The fabric care compositions of the present invention may contain up to about 30%, alternatively from about 0.01% to about 20%, more alternatively from about 0.1% to about 20%, by weight of the composition, of a cationic surfactant. For the purposes of the present invention, cationic surfactants include those which can deliver fabric care benefits. Non-limiting examples of useful cationic surfactants include: fatty amines; quaternary ammonium surfactants; and imidazoline quat materials.

Non-limiting examples of fabric softening actives are N, N-bis(stearoyl-oxy-ethyl) N,N-dimethyl ammonium chloride; N,N-bis(tallowoyl-oxy-ethyl) N,N-dimethyl ammonium chloride, N,N-bis(stearoyl-oxy-ethyl)N-(2 hydroxyethyl)N-methyl ammonium methylsulfate; 1,2 di(stearoyl-oxy) 3 trimethyl ammoniumpropane chloride; dialkylenedimethylammonium salts such as dicanoladimethylammonium chloride, di(hard)tallowdimethylammonium chloride dicanoladimethylammonium methylsulfate; 1-methyl-1-stearoylamidoethyl-2-stearoylimidazolinium methylsulfate; 1-tallowylamidoethyl-2-tallowylimidazoline; N,N"-dialkyldiethylenetriamine; the reaction product of N-(2-hydroxyethyl)-1,2-ethylenediamine or N-(2-hydroxyisopropyl)-1,2-ethylenediamine with glycolic acid, esterified with fatty acid, where the fatty acid is (hydrogenated) tallow fatty acid, palm fatty acid, hydrogenated palm fatty acid, oleic acid, rapeseed fatty acid, hydrogenated rapeseed fatty acid; polyglycerol esters (PGEs), oily sugar derivatives, and wax emulsions and a mixture of the above.

It will be understood that combinations of softener actives disclosed above are suitable for use herein.

Builders—The compositions may also contain from about 0.1% to 80% by weight of a builder. Compositions in liquid form generally contain from about 1% to 10% by weight of the builder component. Compositions in granular form generally contain from about 1% to 50% by weight of the builder component. Detergent builders are well known in the art and can contain, for example, phosphate salts as well as various organic and inorganic nonphosphorus builders. Water-soluble, nonphosphorus organic builders useful herein include the various alkali metal, ammonium and substituted ammonium polyacetates, carboxylates, polycarboxylates and polyhydroxy sulfonates. Examples of polyacetate and polycarboxylate builders are the sodium, potassium, lithium, ammonium and substituted ammonium salts of ethylene diamine tetraacetic acid, nitrilotriacetic acid, oxydisuccinic acid, mellitic acid, benzene polycarboxylic acids, and citric acid. Other polycarboxylate builders are the oxydisuccinates and the ether carboxylate builder compositions comprising a combination of tartrate monosuccinate and tartrate disuccinate. Builders for use in liquid detergents include citric acid. Suitable nonphosphorus, inorganic builders include the silicates, aluminosilicates, borates and carbonates, such as sodium and potassium carbonate, bicarbonate, sesquicarbonate, tetraborate decahydrate, and silicates having a weight ratio of SiO2 to alkali metal oxide of from about 0.5 to about 4.0, or from about 1.0 to about 2.4. Also useful are aluminosilicates including zeolites.

Dispersants—The compositions may contain from about 0.1%, to about 10%, by weight of dispersants. Suitable water-soluble organic materials are the homo- or co-polymeric acids or their salts, in which the polycarboxylic acid may contain at least two carboxyl radicals separated from each other by not more than two carbon atoms. The dispersants may also be alkoxylated derivatives of polyamines, and/or quaternized derivatives.

Enzymes—The compositions may contain one or more detergent enzymes which provide cleaning performance and/or fabric care benefits. Examples of suitable enzymes include hemicellulases, peroxidases, proteases, cellulases, xylanases, lipases, phospholipases, esterases, cutinases, pectinases, keratinases, reductases, oxidases, phenoloxidases, lipoxygenases, ligninases, pullulanases, tannases, pentosanases, malanases, ß-glucanases, arabinosidases, hyaluronidase, chondroitinase, laccase, and amylases, or mixtures thereof. A typical combination may be a cocktail of conventional applicable enzymes like protease, lipase, cutinase and/or cellulase in conjunction with amylase. Enzymes can be used at their art-taught levels, for example at levels recommended by suppliers such as Novozymes and Genencor. Typical levels in the compositions are from about 0.0001% to about 5%. When enzymes are present, they can be used at very low levels, e.g., from about 0.001% or lower; or they can be used in heavier-duty laundry detergent formulations at higher levels, e.g., about 0.1% and higher. In accordance with a preference of some consumers for "non-biological" detergents, the compositions may be either or both enzyme-containing and enzyme-free.

Dye Transfer Inhibiting Agents—The compositions may also include from about 0.0001%, from about 0.01%, from about 0.05% by weight of the compositions to about 10%, about 2%, or even about 1% by weight of the compositions of one or more dye transfer inhibiting agents such as polyvinylpyrrolidone polymers, polyamine N-oxide polymers, copolymers of N-vinylpyrrolidone and N-vinylimidazole, polyvinyloxazolidones and polyvinylimidazoles or mixtures thereof.

Chelant—The compositions may contain less than about 5%, or from about 0.01% to about 3% of a chelant such as citrates; nitrogen-containing, P-free aminocarboxylates such as EDDS, EDTA and DTPA; aminophosphonates such as diethylenetriamine pentamethylenephosphonic acid and, ethylenediamine tetramethylenephosphonic acid; nitrogen-free phosphonates e.g., HEDP; and nitrogen or oxygen containing, P-free carboxylate-free chelants such as compounds of the general class of certain macrocyclic N-ligands such as those known for use in bleach catalyst systems.

Bleach system—Bleach systems suitable for use herein contain one or more bleaching agents. Non-limiting examples of suitable bleaching agents include catalytic metal complexes; activated peroxygen sources; bleach activators; bleach boosters; photobleaches; bleaching enzymes; free radical initiators; $H_2O_2$; hypohalite bleaches; peroxygen sources, including perborate and/or percarbonate and combinations thereof. Suitable bleach activators include perhydrolyzable esters and perhydrolyzable imides such as, tetraacetyl ethylene diamine, octanoylcaprolactam, benzoyloxybenzenesulphonate, nonanoyloxybenzene-isulphonate, benzoylvalerolactam, dodecanoyloxybenzenesulphonate. Other bleaching agents include metal complexes of transitional metals with ligands of defined stability constants.

Stabilizer—The compositions may contain one or more stabilizers and thickeners. Any suitable level of stabilizer may be of use; exemplary levels include from about 0.01% to about 20%, from about 0.1% to about 10%, or from about 0.1% to about 3% by weight of the composition. Non-limiting examples of stabilizers suitable for use herein include crystalline, hydroxyl-containing stabilizing agents, trihydroxystearin, hydrogenated oil, or a variation thereof, and combinations thereof. In some aspects, the crystalline, hydroxyl-containing stabilizing agents may be water-insoluble wax-like substances, including fatty acid, fatty ester or fatty soap. In other aspects, the crystalline, hydroxyl-containing stabilizing agents may be derivatives of castor oil, such as hydrogenated castor oil derivatives, for example, castor wax. Other stabilizers include thickening stabilizers such as gums and other similar polysaccharides, for example gellan gum, carrageenan gum, and other known types of thickeners and rheological additives. Exemplary stabilizers in this class include gum-type polymers (e.g. xanthan gum), polyvinyl alcohol and derivatives thereof, cellulose and derivatives thereof including cellulose ethers and cellulose esters and tamarind gum (for example, comprising xyloglucan polymers), guar gum, locust bean gum (in some aspects comprising galactomannan polymers), and other industrial gums and polymers.

Silicones—Suitable silicones comprise Si—O moieties and may be selected from (a) non-functionalized siloxane polymers, (b) functionalized siloxane polymers, and combinations thereof. The molecular weight of the organosilicone is usually indicated by the reference to the viscosity of the material. The organosilicones may comprise a viscosity of from about 10 to about 2,000,000 centistokes at 25° C. Suitable organosilicones may have a viscosity of from about 10 to about 800,000 centistokes at 25° C.

Suitable organosilicones may be linear, branched or cross-linked.

The organosilicone may comprise a cyclic silicone. The cyclic silicone may comprise a cyclomethicone of the formula $[(CH_3)_2SiO]_n$ where n is an integer that may range from about 3 to about 7, or from about 5 to about 6.

The organosilicone may comprise a functionalized siloxane polymer. Functionalized siloxane polymers may comprise one or more functional moieties selected from the group consisting of amino, amido, alkoxy, hydroxy, polyether, carboxy, hydride, mercapto, sulfate phosphate, and/or quaternary ammonium moieties. These moieties may be attached directly to the siloxane backbone through a bivalent alkylene radical, (i.e., "pendant") or may be part of the backbone. Suitable functionalized siloxane polymers include materials selected from the group consisting of aminosilicones, amidosilicones, silicone polyethers, silicone-urethane polymers, quaternary ABn silicones, amino ABn silicones, and combinations thereof.

The functionalized siloxane polymer may comprise a silicone polyether, also referred to as "dimethicone copolyol." In general, silicone polyethers comprise a polydimethylsiloxane backbone with one or more polyoxyalkylene chains. The polyoxyalkylene moieties may be incorporated in the polymer as pendent chains or as terminal blocks. The functionalized siloxane polymer may comprise an amino-silicone.

The organosilicone may comprise amine ABn silicones and quat ABn silicones. Such organosilicones are generally produced by reacting a diamine with an epoxide.

The functionalized siloxane polymer may comprise silicone-urethanes. These are commercially available from Wacker Silicones under the trade name SLM-21200®.

Perfume: The optional perfume component may comprise a component selected from the group consisting of (1) a perfume containing delivery particle, or a moisture-activated perfume containing delivery particle, comprising a perfume carrier and an encapsulated perfume composition, wherein said perfume carrier may be selected from the group consisting of cyclodextrins, starch microcapsules, porous carrier microcapsules, and mixtures thereof; and wherein said encapsulated perfume composition may comprise low volatile perfume ingredients, high volatile perfume ingredients, and mixtures thereof;

(2) a pro-perfume;

(3) a low odor detection threshold perfume ingredients, wherein said low odor detection threshold perfume ingredients may comprise less than about 25%, by weight of the total neat perfume composition; and (4) mixtures thereof; and Porous Carrier Microcapsule—A portion of the perfume composition can also be absorbed onto and/or into a porous carrier, such as zeolites or clays, to form perfume porous carrier microcapsules in order to reduce the amount of free perfume in the multiple use fabric conditioning composition.

Pro-perfume—The perfume composition may additionally include a pro-perfume. Pro-perfumes may comprise nonvolatile materials that release or convert to a perfume material as a result of, e.g., simple hydrolysis, or may be pH-change-triggered pro-perfumes (e.g. triggered by a pH drop) or may be enzymatically releasable pro-perfumes, or light-triggered pro-perfumes. The pro-perfumes may exhibit varying release rates depending upon the pro-perfume chosen.

Fabric Hueing Agents—The composition may comprise a fabric hueing agent (sometimes referred to as shading, bluing or whitening agents). Typically the hueing agent provides a blue or violet shade to fabric. Hueing agents can be used either alone or in combination to create a specific shade of hueing and/or to shade different fabric types. This may be provided for example by mixing a red and a green-blue dye to yield a blue or violet shade. Hueing agents may be selected from any known chemical class of dyes, including but not limited to acridine, anthraquinone (including polycyclic quinones), azine, azo (e.g., monoazo, disazo, trisazo, tetrakisazo, polyazo), including premetallized azo, benzodifurane and benzodifuranone, carotenoid, coumarin, cyanine, diazahemicyanine, diphenylmethane, formazan, hemicyanine, indigoids, methane, naphthalimides, naphthoquinone, nitro and nitroso, oxazine, phthalocyanine, pyrazoles, stilbene, styryl, triarylmethane, triphenylmethane, xanthenes and mixtures thereof. Suitable fabric hueing agents include dyes, dye-clay conjugates, and organic and inorganic pigments. Suitable dyes include small molecule dyes and polymeric dyes. Suitable small molecule dyes include small molecule dyes selected from the group consisting of dyes falling into the Colour Index (C.I.) classifications of Acid, Direct, Basic, Reactive or hydrolysed Reactive, Solvent or Disperse dyes for example that are classified as Blue, Violet, Red, Green or Black, and provide the desired shade either alone or in combination. Suitable small molecule dyes include small molecule dyes selected from the group consisting of Colour Index (Society of Dyers and Colourists, Bradford, UK) numbers Direct Violet dyes such as 9, 35, 48, 51, 66, and 99, Direct Blue dyes such as 1, 71, 80 and 279, Acid Red dyes such as 17, 73, 52, 88 and 150, Acid Violet dyes such as 15, 17, 24, 43, 49 and 50, Acid Blue dyes such as 15, 17, 25, 29, 40, 45, 75, 80, 83, 90 and 113, Acid Black dyes such as 1, Basic Violet dyes such as 1, 3, 4, 10 and 35, Basic Blue dyes such as 3, 16, 22, 47, 66, 75 and 159, Disperse or Solvent dyes U.S. Pat. No. 8,268,016 B2, or dyes as disclosed in U.S. Pat. No. 7,208,459 B2, and mixtures thereof. Suitable small molecule dyes include small molecule dyes selected from the group consisting of C. I. numbers Acid Violet 17, Acid Blue 80, Acid Violet 50, Direct Blue 71, Direct Violet 51, Direct Blue 1, Acid Red 88, Acid Red 150, Acid Blue 29, Acid Blue 113 or mixtures thereof.

Suitable polymeric dyes include polymeric dyes selected from the group consisting of polymers containing covalently bound (sometimes referred to as conjugated) chromogens, (dye-polymer conjugates), for example polymers with chromogens co-polymerized into the backbone of the polymer and mixtures thereof. Polymeric dyes include those described in U.S. Pat. No. 7,686,892 B2.

Suitable polymeric dyes include polymeric dyes selected from the group consisting of fabric-substantive colorants sold under the name of Liquitint® (Milliken, Spartanburg, South Carolina, USA), dye-polymer conjugates formed from at least one reactive dye and a polymer selected from the group consisting of polymers comprising a moiety selected from the group consisting of a hydroxyl moiety, a primary amine moiety, a secondary amine moiety, a thiol moiety and mixtures thereof. Suitable polymeric dyes include polymeric dyes selected from the group consisting of Liquitint® Violet C T, carboxymethyl cellulose (CMC) covalently bound to a reactive blue, reactive violet or reactive red dye such as CMC conjugated with C.I. Reactive Blue 19, sold by Megazyme, Wicklow, Ireland under the product name AZO-CM-CELLULOSE, product code S-ACMC, alkoxylated triphenyl-methane polymeric colourants, alkoxylated thiophene polymeric colourants, and mixtures thereof.

Suitable dye clay conjugates include dye clay conjugates selected from the group comprising at least one cationic/basic dye and a smectite clay, and mixtures thereof. Suitable dye clay conjugates include dye clay conjugates selected from the group consisting of one cationic/basic dye selected from the group consisting of C.I. Basic Yellow 1 through 108, C.I. Basic Orange 1 through 69, C.I. Basic Red 1 through 118, C.I. Basic Violet 1 through 51, C.I. Basic Blue 1 through 164, C.I. Basic Green 1 through 14, C.I. Basic Brown 1 through 23, CI Basic Black 1 through 11, and a clay selected from the group consisting of Montmorillonite clay, Hectorite clay, Saponite clay and mixtures thereof. Suitable dye clay conjugates include dye clay conjugates selected from the group consisting of: Montmorillonite Basic Blue B7 C.I. 42595 conjugate, Montmorillonite Basic Blue B9 C.I. 52015 conjugate, Montmorillonite Basic Violet V3 C.I. 42555 conjugate, Montmorillonite Basic Green G1 C.I. 42040 conjugate, Montmorillonite Basic Red R1 C.I. 45160 conjugate, Montmorillonite C.I. Basic Black 2 conjugate, Hectorite Basic Blue B7 C.I. 42595 conjugate, Hectorite Basic Blue B9 C.I. 52015 conjugate, Hectorite Basic Violet V3 C.I. 42555 conjugate, Hectorite Basic Green G1 C.I. 42040 conjugate, Hectorite Basic Red R1 C.I. 45160 conjugate, Hectorite C.I. Basic Black 2 conjugate, Saponite Basic Blue B7 C.I. 42595 conjugate, Saponite Basic Blue B9 C.I. 52015 conjugate, Saponite Basic Violet V3 C.I. 42555 conjugate, Saponite Basic Green G1 C.I. 42040 conjugate, Saponite Basic Red R1 C.I. 45160 conjugate, Saponite C.I. Basic Black 2 conjugate and mixtures thereof.

The hueing agent may be incorporated into the detergent composition as part of a reaction mixture which is the result of the organic synthesis for a dye molecule, with optional purification step(s). Such reaction mixtures generally comprise the dye molecule itself and in addition may comprise un-reacted starting materials and/or by-products of the organic synthesis route.

Suitable polymeric bluing agents may be alkoxylated. As with all such alkoxylated compounds, the organic synthesis may produce a mixture of molecules having different degrees of alkoxylation. Such mixtures may be used directly to provide the hueing agent, or may undergo a purification step to increase the proportion of the target molecule.

Suitable pigments include pigments selected from the group consisting of flavanthrone, indanthrone, chlorinated indanthrone containing from 1 to 4 chlorine atoms, pyranthrone, dichloropyranthrone, monobromodichloropyranthrone, dibromodichloropyranthrone, tetrabromopyranthrone, perylene-3,4,9,10-tetracarboxylic acid diimide, wherein the imide groups may be unsubstituted or substituted by $C_1$-$C_3$-alkyl or a phenyl or heterocyclic radical, and wherein the phenyl and heterocyclic radicals may additionally carry substituents which do not confer solubility in water, anthrapyrimidinecarboxylic acid amides, violanthrone, isoviolanthrone, dioxazine pigments, copper phthalocyanine which may contain up to 2 chlorine atoms per molecule, polychloro-copper phthalocyanine or polybromochloro-copper phthalocyanine containing up to 14 bromine atoms per molecule and mixtures thereof. Suitable pigments include pigments selected from the group consisting of Ultramarine Blue (C.I. Pigment Blue 29), Ultramarine Violet (C.I. Pigment Violet 15), Monastral Blue and mixtures thereof. The aforementioned fabric hueing agents can be used in combination (any mixture of fabric hueing agents can be used).

Structurants—Useful structurant materials that may be added to adequately suspend the benefit agent containing delivery particles include polysaccharides, for example, gellan gum, waxy maize or dent corn starch, octenyl succinated starches, derivatized starches such as hydroxyethylated or hydroxypropylated starches, carrageenan, guar gum, pectin, xanthan gum, and mixtures thereof; modified celluloses such as hydrolyzed cellulose acetate, hydroxy propyl cellulose, methyl cellulose, and mixtures thereof; modified proteins such as gelatin; hydrogenated and non-hydrogenated polyalkenes, and mixtures thereof; inorganic salts, for example, magnesium chloride, calcium chloride, calcium formate, magnesium formate, aluminum chloride, potassium permanganate, laponite clay, bentonite clay and mixtures thereof; polysaccharides in combination with inorganic salts; quaternized polymeric materials, for example, polyether amines, alkyl trimethyl ammonium chlorides, diester ditallow ammonium chloride; imidazoles; nonionic polymers with a pKa less than 6.0, for example polyethyleneimine, polyethyleneimine ethoxylate; polyurethanes. Such materials can be obtained from CP Kelco Corp. of San Diego, California, USA; Degussa A G or Dusseldorf, Germany; BASF AG of Ludwigshafen, Germany; Rhodia Corp. of Cranbury, New Jersey, USA; Baker Hughes Corp. of Houston, Texas, USA; Hercules Corp. of Wilmington, Delaware, USA; Agrium Inc. of Calgary, Alberta, Canada, ISP of New Jersey, U.S.A.

Anti-agglomeration agents—Useful anti-agglomeration agent materials include, divalent salts such as magnesium salts, for example, magnesium chloride, magnesium acetate, magnesium phosphate, magnesium formate, magnesium boride, magnesium titanate, magnesium sulfate heptahydrate; calcium salts, for example, calcium chloride, calcium formate, calcium acetate, calcium bromide; trivalent salts, such as aluminum salts, for example, aluminum sulfate, aluminum phosphate, aluminum chloride hydrate and polymers that have the ability to suspend anionic particles such as suspension polymers, for example, polyethylene imines, alkoxylated polyethylene imines, polyquaternium-6 and polyquaternium-7.

Coatings—Benefit agent containing delivery particles may be manufactured and subsequently coated with an additional material. Non-limiting examples of coating materials include but are not limited to materials selected from the group consisting of poly(meth)acrylate, poly(ethylene-maleic anhydride), polyamine, wax, polyvinylpyrrolidone, polyvinylpyrrolidone co-polymers, polyvinylpyrrolidone-ethyl acrylate, polyvinylpyrrolidone-vinyl acrylate, polyvinylpyrrolidone methylacrylate, polyvinylpyrrolidone/vinyl acetate, polyvinyl acetal, polyvinyl butyral, polysiloxane, poly(propylene maleic anhydride), maleic anhydride derivatives, co-polymers of maleic anhydride derivatives, polyvinyl alcohol, styrene-butadiene latex, gelatin, gum Arabic, carboxymethyl cellulose, carboxymethyl hydroxyethyl cellulose, hydroxyethyl cellulose, other modified celluloses, sodium alginate, chitosan, casein, pectin, modified starch, polyvinyl acetal, polyvinyl butyral, polyvinyl methyl ether/maleic anhydride, polyvinyl pyrrolidone and its co polymers, poly(vinyl pyrrolidone/methacrylamidopropyl trimethyl ammonium chloride), polyvinylpyrrolidone/vinyl acetate, polyvinyl pyrrolidone/dimethylaminoethyl methacrylate, polyvinyl amines, polyvinyl formamides, polyallyl amines and copolymers of polyvinyl amines, polyvinyl formamides, and polyallyl amines and mixtures thereof. Such materials can be obtained from CP Kelco Corp. of San Diego, California, USA; Degussa A G or Dusseldorf, Germany; BASF AG of Ludwigshafen, Germany; Rhodia Corp. of Cranbury, New Jersey, USA; Baker Hughes Corp. of Houston, Texas, USA; Hercules Corp. of Wilmington, Delaware, USA; Agrium Inc. of Calgary, Alberta, Canada, ISP of New Jersey U.S.A.

Malodor Reduction Materials

The compositions of the present invention may comprise malodor reduction materials. Such materials are capable of decreasing or even eliminating the perception of one or more malodors.

The compositions of the present invention may comprise a sum total of from about 0.00025% to about 0.5%, preferably from about 0.0025% to about 0.1%, more preferably from about 0.005% to about 0.075%, most preferably from about 0.01% to about 0.05%, by weight of the composition, of 1 or more malodor reduction materials. The compositions may comprise from about 1 to about 20 malodor reduction materials, more preferably 1 to about 15 malodor reduction materials, most preferably 1 to about 10 malodor reduction materials.

The compositions of the present invention may comprise a perfume to provide hedonic benefits. The weight ratio of parts of malodor reduction composition to parts of perfume may be from about 1:20,000 to about 3,000:1, preferably from about 1:10,000 to about 1,000:1, more preferably from about 5,000:1 to about 500:1, and most preferably from about 1:15 to about 1:1. As the ratio of malodor reduction composition to parts of perfume is tightened, the malodor reduction material(s) provide less and less of a scent impact, while continuing to counteract malodors.

The compositions may comprise one or more malodor reduction materials having a log P greater than 3, preferably greater than 3 but less than 11. The one or more malodor reduction materials may be selected from the group consisting of Table 2 materials 7; 14; 39; 48; 183; 185; 195; 206; 212; 215; 227; 228; 229; 230; 231; 248; 260; 261; 276; 289; 335; 343; 360; 391; 428; 441; 484; 487; 488; 501; 520; 566; 567; 569; 570; 572; 573; 574; 592; 603; 616; 621; 624; 627; 632; 644; 663; 677; 679; 680; 684; 694; 696; 700; 704; 708; 712; 714; 722; 723; 726; 750; 769; 775; 776; 788; 804; 872; 912; 919; 925; 927; 933; 978; 1007; 1022; 1024; 1029; 1035; 1038; 1060; 1073; 1077; 1089; 1107; 1129; 1131; 1137; 1140; 1142; 1143; 1144; 1145; 1148; 1149; 1152; 1153; 1154 and mixtures thereof, most preferably said material is selected from the group consisting of Table 2 materials 185; 215; 260; 261; 276; 289; 335; 391; 428; 441; 501; 520; 572; 573; 592; 627; 677; 700; 769; 788; 912; 919; 925; 1073; 1129; 1148; 1149; 1152; 1153; 1154 and mixtures thereof. All of the aforementioned materials have a log P that is equal to or greater than 3 but less than 11, thus they deposit through the wash especially well. The more preferred and most preferred of the aforementioned material are particularly preferred as they are effective at counteracting all of the key malodors.

A non-limiting set of suitable malodor reduction materials are provided in Table 2 below. The compositions described herein may comprise a malodor reduction material selected from any of the materials listed in Table 2, or combinations thereof. For ease of reference herein, each material in Table 2 is assigned a numerical identifier which is found in the column for each table that is designated Number.

TABLE 2

List of materials

| Number | Material Name | CAS Number |
|---|---|---|
| 7 | 3-methoxy-7,7-dimethyl-10-methylenebicyclo[4.3.1]decane | 216970-21-7 |
| 14 | Oxyoctaline formate | 65405-72-3 |
| 39 | 2,2,6,8-tetramethyl-1,2,3,4,4a,5,8,8a-octahydronaphthalen-1-ol | 103614-86-4 |
| 48 | Nootkatone | 4674-50-4 |
| 183 | Khusimol | 16223-63-5 |
| 185 | (1-methyl-2-((1,2,2-trimethylbicyclo[3.1.0]hexan-3-yl)methyl)cyclopropyl)methanol | 198404-98-7 |
| 195 | Isopropyl palmitate | 142-91-6 |
| 206 | Iso3-methylcyclopentadecan-1-one | 3100-36-5 |
| 212 | Isoeugenyl benzyl ether | 120-11-6 |
| 215 | 1-((2S,3S)-2,3,8,8-tetramethyl-1,2,3,4,5,6,7,8-octahydronaphthalen-2-yl)ethan-1-one | 54464-57-2 |
| 227 | Isobornylcyclohexanol | 68877-29-2 |
| 228 | Isobornyl propionate | 2756-56-1 |
| 229 | Isobornyl isobutyrate | 85586-67-0 |
| 230 | Isobornyl cyclohexanol | 66072-32-0 |
| 231 | (1R,4S)-1,7,7-trimethylbicyclo[2.2.1]heptan-2-yl acetate | 125-12-2 |
| 233 | Isobergamate | 68683-20-5 |
| 248 | Hydroxymethyl isolongifolene | 59056-64-3 |
| 260 | 2,3-dihydro-3,3-dimethyl-1H-indene-5-propanal | 173445-44-8 |
| 261 | 3-(3,3-dimethyl-2,3-dihydro-1H-inden-5-yl)propanal | 173445-65-3 |
| 276 | (E)-3,7-dimethylocta-2,6-dien-1-yl palmitate | 3681-73-0 |
| 289 | (E)-oxacyclohexadec-13-en-2-one | 111879-80-2 |
| 329 | gamma-Eudesmol | 1209-71-8 |

TABLE 2-continued

List of materials

| Number | Material Name | CAS Number |
|---|---|---|
| 335 | 4,6,6,7,8,8-hexamethyl-1,3,4,6,7,8-hexahydrocyclopenta[g]isochromene | 1222-05-5 |
| 343 | 8,8-dimethyl-3a,4,5,6,7,7a-hexahydro-1H-4,7-methanoinden-6-yl propionate | 76842-49-4 |
| 360 | 8,8-dimethyl-3a,4,5,6,7,7a-hexahydro-1H-4,7-methanoinden-6-yl acetate | 171102-41-3 |
| 391 | Ethyl dodecanoate | 106-33-2 |
| 428 | oxydibenzene | 101-84-8 |
| 441 | Octahydro-1H-4,7-methanoinden-5-yl acetate | 64001-15-6 |
| 484 | 3a,4,5,6,7,7a-hexahydro-1H-4,7-methanoinden-6-yl butyrate | 113889-23-9 |
| 487 | 3a,4,5,6,7,7a-hexahydro-1H-4,7-methanoinden-5-yl isobutyrate | 67634-20-2 |
| 488 | Curzerene | 17910-09-7 |
| 501 | (E)-cycloheptadec-9-en-1-one | 542-46-1 |
| 520 | (E)-1,1-dimethoxy-3,7-dimethylocta-2,6-diene | 7549-37-3 |
| 566 | Cedryl formate | 39900-38-4 |
| 567 | Cedryl acetate | 77-54-3 |
| 569 | Cedrol | 77-53-2 |
| 570 | 5-methyl-1-(2,2,3-trimethylcyclopent-3-en-1-yl)-6-oxabicyclo[3.2.1]octane | 139539-66-5 |
| 572 | 1,1,2,3,3-pentamethyl-1,2,3,5,6,7-hexahydro-4H-inden-4-one | 33704-61-9 |
| 573 | Caryophyllene alcohol acetate | 32214-91-8 |
| 574 | Caryolan-1-ol | 472-97-9 |
| 592 | 2,6-di-tert-butyl-4-methylphenol | 128-37-0 |
| 603 | Bornyl isobutyrate | 24717-86-0 |
| 616 | beta-Santalol | 77-42-9 |
| 621 | beta-Patchoulline | 514-51-2 |
| 624 | beta-Himachalene Oxide | 57819-73-5 |
| 627 | (2,2-dimethoxyethyl)benzene | 101-48-4 |
| 632 | beta-Cedrene | 546-28-1 |
| 644 | Benzyl laurate | 140-25-0 |
| 663 | Anisyl phenylacetate | 102-17-0 |
| 677 | 1-((2-(tert-butyl)cyclohexyl)oxy)butan-2-ol | 139504-68-0 |
| 679 | 2,2,6,6,7,8,8-heptamethyldecahydro-2H-indeno[4,5-b]furan | 476332-65-7 |
| 680 | 2,2,6,6,7,8,8-heptamethyldecahydro-2H-indeno[4,5-b]furan | 647828-16-8 |
| 684 | alpha-Vetivone | 15764-04-2 |
| 694 | alpha-Santalol | 115-71-9 |
| 696 | alpha-Patchoulene | 560-32-7 |
| 700 | alpha-methyl ionone | 127-42-4 |
| 704 | alpha-Irone | 79-69-6 |
| 708 | alpha-Gurjunene | 489-40-7 |
| 712 | alpha-Eudesmol | 473-16-5 |
| 714 | alpha-Cubebene | 17699-14-8 |
| 722 | alpha-Amylcinnamyl acetate | 7493-78-9 |
| 723 | alpha-Amylcinnamaldehyde diethyl acetal | 60763-41-9 |
| 726 | alpha-Agarofuran | 5956-12-7 |
| 750 | Allo-aromadendrene | 25246-27-9 |
| 769 | (Z)-2-(4-methylbenzylidene)heptanal | 84697-09-6 |
| 775 | 7-eip-alpha-Eudesmol | 123123-38-6 |
| 776 | 7-Acetyl-1,1,3,4,4,6-hexamethyltetralin | 1506-02-1 |
| 788 | 5-Cyclohexadecenone | 37609-25-9 |
| 804 | 3-Thujopsanone | 25966-79-4 |
| 872 | 10-epi-gamma-Eudesmol | 15051-81-7 |
| 912 | 2-(8-isopropyl-6-methylbicyclo[2.2.2]oct-5-en-2-yl)-1,3-dioxolane | 68901-32-6 |
| 919 | 3a,4,5,6,7,7a-hexahydro-1H-4,7-methanoinden-6-yl propionate | 17511-60-3 |
| 925 | 3-(6,6-dimethylbicyclo[3.1.1]hept-2-en-2-yl)-2,2-dimethylpropanal | 33885-52-8 |
| 927 | 5-Acetyl-1,1,2,3,3,6-hexamethylindan | 15323-35-0 |
| 933 | Patchouli alcohol | 5986-55-0 |
| 978 | 3a,4,5,6,7,7a-hexahydro-1H-4,7-methanoinden-6-yl pivalate | 68039-44-1 |
| 1007 | (2R,4a'R,8a'R)-3,7'-dimethyl-3',4',4a',5',8',8a'-hexahydro-1'H-spiro[oxirane-2,2'-[1,4]methanonaphthalene] | 41816-03-9 |

TABLE 2-continued

| List of materials | | |
|---|---|---|
| Number | Material Name | CAS Number |
| 1022 | 2,2,7,9-tetramethylspiro(5.5)undec-8-en-1-one | 502847-01-0 |
| 1024 | (Z)-2-ethyl-4-(2,2,3-trimethylcyclopent-3-en-1-yl)but-2-en-1-ol | 28219-61-6 |
| 1029 | Sclareol oxide | 5153-92-4 |
| 1035 | Spathulenol | 6750-60-3 |
| 1038 | 1-(spiro[4.5]dec-7-en-7-yl)pent-4-en-1-one | 224031-70-3 |
| 1060 | Thujopsene | 470-40-6 |
| 1073 | (E)-dec-4-enal | 65405-70-1 |
| 1077 | (Z)-3,7-dimethylocta-1,3,6-triene | 13877-91-3 |
| 1089 | Tricyclone | 68433-81-8 |
| 1107 | Valerianol | 20489-45-6 |
| 1129 | 1-((3R,3aR,7R,8aS)-3,6,8,8-tetramethyl-2,3,4,7,8,8a-hexahydro-1H-3a,7-methanoazulen-5-yl)ethan-1-one | 32388-55-9 |
| 1131 | Methyl(Z)-2-(((2,4-dimethylcyclohex-3-en-1-yl)methylene)amino)benzoate | 68738-99-8 |
| 1137 | Decahydro-3H-spiro[furan-2,5'-[4,7]methanoindene] | 68480-11-5 |
| 1140 | (1aR,4S,4aS,7R,7aS,7bS)-1,1,4,7-tetramethyldecahydro-1H-cyclopropa[e]azulen-4-ol | 552-02-3 |
| 1142 | 3,5,5,6,7,8,8-heptamethyl-5,6,7,8-tetrahydronaphthalene-2-carbonitrile | 127459-79-4 |
| 1143 | (1S,2S,3S,5R)-2,6,6-trimethylspiro[bicyclo[3.1.1]heptane-3,1'-cyclohexan]-2'-en-4'-one | 133636-82-5 |
| 1144 | 1',1',5',5'-tetramethylhexahydro-2'H,5'H-spiro[[1,3]dioxolane-2,8'-[2,4a]methanonaphthalene] | 154171-76-3 |
| 1145 | 1',1',5',5'-tetramethylhexahydro-2'H,5'H-spiro[[1,3]dioxolane-2,8'-[2,4a]methanonaphthalene] K | 154171-77-4 |
| 1148 | 4,5-epoxy-4,11,11-trimethyl-8-methylenebicyclo(7.2.0)undecane | 1139-30-6 |
| 1149 | 1,3,4,6,7,8alpha-hexahydro-1,1,5,5-tetramethyl-2H-2,4alpha-methanophtalen-8(5H)-one | 23787-90-8 |
| 1152 | 1,1-dimethyl-2,3-dihydro-1H-indene-ar-propanal | 300371-33-9 |
| 1153 | 3a,4,5,6,7,7a-hexahydro-1H-4,7-methanoinden-1-yl propanoate | 68912-13-0 |
| 1154 | 4,8-Dimethyl-1-(Methylethyl)-7-Oxabicyclo[4.3.0] Nonane | TBD |

The materials in Table 2 can be supplied by one or more of the following: Firmenich Inc. of Plainsboro NJ USA; International Flavor and Fragrance Inc. New York, NY USA; Takasago Corp. Teterboro, NJ USA; Symrise Inc. Teterboro, NJ USA; Sigma-Aldrich/SAFC Inc. Carlsbad, CA USA; and Bedoukian Research Inc., Danbury, CT USA.

Method of Use and Treated Situs

Compositions containing the benefit agent containing delivery particle disclosed herein can be used to clean or treat a situs inter alia a surface or fabric. Typically at least a portion of the situs is contacted with an embodiment of Applicants' composition, in neat form or diluted in a liquor, for example, a wash liquor and then the situs may be optionally washed and/or rinsed A method of treating and/or cleaning a situs, said method comprising a) optionally washing, rinsing and/or drying said situs;
b) contacting said situs with a consumer product according to any of Paragraphs (A) through (M) of this specification and/or made by the process of Paragraph (A1) of this specification; and
c) optionally washing, rinsing and/or drying said situs wherein said drying steps comprise active drying and/or passive drying, is disclosed.

For purposes of the present invention, washing includes but is not limited to, scrubbing, and mechanical agitation. The fabric may comprise any fabric capable of being laundered or treated in normal consumer use conditions. Liquors that may comprise the disclosed compositions may have a pH of from about 3 to about 11.5. Such compositions are typically employed at concentrations of from about 500 ppm to about 15,000 ppm in solution. When the wash solvent is water, the water temperature typically ranges from about 5° C. to about 90° C. and, when the situs comprises a fabric, the water to fabric ratio is typically from about 1:1 to about 30:1.

A situs treated with any embodiment of any composition disclosed herein is disclosed.

A situs treated with a consumer product according to any of Paragraphs (A) through (M) of this specification and/or made by the process of Paragraph (A1) of this specification, is disclosed.

Test Methods

It is understood that the test methods that are disclosed in the Test Methods Section of the present application should be used to determine the respective values of the parameters of Applicants' invention as such invention is described and claimed herein.

(1) Extraction of Benefit Agent Containing Delivery Particles from Finished Products Except where otherwise specified herein, the preferred method to isolate benefit agent containing delivery particles from finished products is based on the fact that the density of most such particles is different from that of water. The finished product is mixed with water in order to dilute and/or release the particles. The diluted product suspension is centrifuged to speed up the separation of the particles. Such particles tend to float or sink in the diluted solution/dispersion of the finished product. Using a pipette or spatula, the top and bottom layers of this suspension are removed, and undergo further rounds of dilution and centrifugation to separate and enrich the particles. The particles are observed using an optical microscope equipped with crossed-polarized filters or differential interference contrast (DIC), at total magnifications of 100× and 400×. The microscopic observations provide an initial indication of the presence, size, quality and aggregation of the delivery particles.

For extraction of delivery particles from a liquid fabric enhancer finished product conduct the following procedure:

1. Place three aliquots of approximately 20 ml of liquid fabric enhancer into three separate 50 ml centrifuge tubes and dilute each aliquot 1:1 with DI water (eg 20 ml fabric enhancer+20 ml DI water), mix each aliquot well and centrifuge each aliquot for 30 minutes at approximately 10000×g.
2. After centrifuging per Step 1, discard the bottom water layer (around 10 ml) in each 50 ml centrifuge tube then add 10 ml of DI water to each 50 ml centrifuge tube.
3. For each aliquot, repeat the process of centrifuging, removing the bottom water layer and then adding 10 ml of DI water to each 50 ml centrifuge tube two additional times.
4. Remove the top layer with a spatula or a pipette.
5. Transfer this top layer into a 1.8 ml centrifuge tube and centrifuge for 5 minutes at approximately 20000×g.
6. Remove the top layer with a spatula and transfer into a new 1.8 ml centrifuge tube and add DI water until the tube is completely filled, then centrifuge for 5 minutes at approximately 20000×g.

7. Remove the bottom layer with a fine pipette and add DI water until tube is completely filled and centrifuge for 5 minutes at approximately 20000×g.
8. Repeat step 7 for an additional 5 times (6 times in total).

If both a top layer and a bottom layer of enriched particles appear in the above described step 1, then, immediately move to step 3 (i.e., omit step 2) and proceed steps with steps 4 through 8. Once those steps have been completed, also remove the bottom layer from the 50 ml centrifuge tube from step 1, using a spatula or/and a pipette. Transfer the bottom layer into a 1.8 ml centrifuge tube and centrifuge 5 min at approximately 20000×g. Remove the bottom layer in a new tube and add DI water until the tube is completely filled then centrifuge for 5 minutes approximately 20000×g. Remove the top layer (water) and add DI water again until the tube is full. Repeat this another 5 times (6 times in total). Recombine the particle enriched and isolated top and bottom layers back together.

If the fabric enhancer has a white color or is difficult to distinguish the particle enriched layers add 4 drops of dye (such as Liquitint Blue JH 5% premix from Milliken & Company, Spartanburg, South Carolina, USA) into the centrifuge tube of step 1 and proceed with the isolation as described.

For extraction of delivery particles from solid finished products which disperse readily in water, mix 1 L of DI water with 20 g of the finished product (eg. detergent foams, films, gels and granules; or water-soluble polymers; soap flakes and soap bars; and other readily water-soluble matrices such as salts, sugars, clays, and starches). When extracting particles from finished products which do not disperse readily in water, such as waxes, dryer sheets, dryer bars, and greasy materials, it may be necessary to add detergents, agitation, and/or gently heat the product and diluent in order to release the particles from the matrix. The use of organic solvents or drying out of the particles should be avoided during the extraction steps as these actions may damage the delivery particles during this phase.

For extraction of delivery particles from liquid finished products which are not fabric softeners or fabric enhancers (eg., liquid laundry detergents, liquid dish washing detergents, liquid hand soaps, lotions, shampoos, conditioners, and hair dyes), mix 20 ml of finished product with 20 ml of DI water. If necessary, NaCl (eg., 100-200 g NaCl) can be added to the diluted suspension in order to increase the density of the solution and facilitate the particles floating to the top layer. If the product has a white color which makes it difficult to distinguish the layers of particles formed during centrifugation, a water-soluble dye can be added to the diluent to provide visual contrast. The water and product mixture is subjected to sequential rounds of centrifugation, involving removal of the top and bottom layers, re-suspension of those layers in new diluent, followed by further centrifugation, isolation and re-suspension. Each round of centrifugation occurs in tubes of 1.5 to 50 ml in volume, using centrifugal forces of up to 20,000×g, for periods of 5 to 30 minutes. At least six rounds of centrifugation are typically needed to extract and clean sufficient particles for testing. For example, the initial round of centrifugation may be conducted in 50 ml tubes spun at 10,000×g for 30 mins, followed by five more rounds of centrifugation where the material from the top and bottom layers is resuspended separately in fresh diluent in 1.8 ml tubes and spun at 20,000×g for 5 mins per round.

If delivery particles are observed microscopically in both the top and bottom layers, then the particles from these two layers are recombined after the final centrifugation step, to create a single sample containing all the delivery particles extracted from that product. The extracted particles should be analyzed as soon as possible but may be stored as a suspension in DI water for up to 14 days before they are analyzed.

One skilled in the art will recognize that various other protocols may be constructed for the extraction and isolation of delivery particles from finished products, and will recognize that such methods require validation via a comparison of the resulting measured values, as measured before and after the particles' addition to and extraction from finished product.

(2) Particle Size (Diameter)

A drop of the particle suspension or finished product is placed onto a glass microscope slide and dried under ambient conditions for several minutes to remove the water and achieve a sparse, single layer of solitary particles on the dry slide. Adjust the concentration of particles in the suspension as needed to achieve a suitable particle density on the slide. The slide is placed on a sample stage of an optical microscope equipped and examined at a total magnification of 100× or 400×. Images are captured and calibrated for the accurate measurement of particle diameters. Three replicate slides are prepared and analyzed.

For particle size measurement, at least 50 benefit agent delivery particles on each slide are selected for measurement, in a manner which is unbiased by their size and so creates a representative sample of the distribution of particle sizes present. This may be achieved by examining fields-of-view which are selected at random or according to a pre-defined grid pattern, and by measuring the diameter of all the delivery particles present in each field-of-view examined. Delivery particles which appear obviously non-spherical, deflated, leaking, or damaged are unsuitable for measurement, are excluded from the selection process and their diameters are not recorded. The diameter of each suitable delivery particle examined is measured using the microscope and the value is recorded. The recorded particle diameter measurements are used to calculate the percentage of the particles having a particle size within the claimed size range(s), and also to calculate the mean particle size.

(3) Particle Shell Thickness

The particle shell thickness is measured in nanometers on 50 benefit agent containing delivery particles using freeze-fracture cryo-scanning electron microscopy (FF cryoSEM), at magnifications of between 50,000× and 150,000×. Samples are prepared by flash freezing small volumes of a suspension of particles or finished product. Flash freezing can be achieved by plunging into liquid ethane, or through the use of a device such as a High Pressure Freezer Model 706802 EM Pact, (Leica Microsystems, Wetzlar, Germany). Frozen samples are fractured while at −120° C., then cooled to below −160° C. and lightly sputter-coated with gold/palladium. These steps can be achieved using cryo preparation devices such as those from Gatan Inc., (Pleasanton, CA, USA). The frozen, fractured and coated sample is then transferred at −170° C. or lower, to a suitable cryoSEM microscope, such as the Hitachi S-5200 SEM/STEM (Hitachi High Technologies, Tokyo, Japan). In the Hitachi S-5200, imaging is performed with 3.0 KV accelerating voltage and 5 μA-20 μA tip emission current.

Images are acquired of the fractured shell in cross-sectional view from 50 benefit agent containing delivery particles selected in a random manner which is unbiased by their size, so as to create a representative sample of the distribution of particle sizes present. The shell thickness of each of the 50 particles is measured using the calibrated microscope software, by drawing a measurement line perpendicular to the outer surface of the particle shell. The 50 independent shell thickness measurements are recorded and used to calculate the mean thickness, and the percentage of the particles having a shell thickness within the claimed range.

(4) Benefit Agent Leakage

The amount of benefit agent leakage from the benefit agent containing delivery particles is determined according to the following method:

a.) Obtain two 1 g samples of the raw material slurry of benefit agent containing delivery particles.
b.) Add 1 g of the raw material slurry of benefit agent containing delivery particles to 99 g of the product matrix in which the particles will be employed, and label the mixture as Sample 1. Immediately use the second 1 g sample of raw material particle slurry in Step d below, in its neat form without contacting product matrix, and label it as Sample 2.
c.) Age the particle-containing product matrix (Sample 1) for 2 weeks at 35° C. in a sealed, glass jar.
d.) Using filtration, recover the particles from both samples. The particles in Sample 1 (in product matrix) are recovered after the aging step. The particles in Sample 2 (neat raw material slurry) are recovered at the same time that the aging step began for sample 1.
e.) Treat the recovered particles with a solvent to extract the benefit agent materials from the particles.
f.) Analyze the solvent containing the extracted benefit agent from each sample, via chromatography. Integrate the resultant benefit agent peak areas under the curve, and sum these areas to determine the total quantity of benefit agent extracted from each sample.
g.) Determine the percentage of benefit agent leakage by calculating the difference in the values obtained for the total quantity of benefit agent extracted from Sample 2 minus Sample 1, expressed as a percentage of the total quantity of benefit agent extracted from Sample 2, as represented in the equation below:

$$\text{Percentage of Benefit Agent Leakage} = \left(\frac{\text{Sample 2} - \text{Sample 1}}{\text{Sample 2}}\right) \times 100$$

(5) Viscosity

Viscosity of liquid finished product is measured using an AR 550 rheometer/viscometer from TA instruments (New Castle, DE, USA), using parallel steel plates of 40 mm diameter and a gap size of 500 μm. The high shear viscosity at 20 $s^{-1}$ and low shear viscosity at 0.05 $s^{-1}$ is obtained from a logarithmic shear rate sweep from 0.1 $s^{-1}$ to 25 $s^{-1}$ in 3 minutes time at 21° C.

(6) Perfume and Perfume Raw Materials (PRMs)

To determine the identity and to quantify the weight of perfume, perfume ingredients, or Perfume Raw Materials (PRMs), encapsulated within the benefit agent containing delivery particles, Gas Chromatography with Mass Spectroscopy/Flame Ionization Detector (GC-MS/FID) is employed. Suitable equipment includes: Agilent Technologies G1530A GC/FID; Hewlett Packard Mass Selective Device 5973; and 5%-Phenyl-methylpolysiloxane Column J&W DB-5 (30 m length×0.25 mm internal diameter×0.25 μm film thickness). Approximately 3 g of the finished product or suspension of delivery particles, is weighed and the weight recorded, then the sample is diluted with 30 mL of DI water and filtered through a 5.0 μm pore size nitrocellulose filter membrane. Material captured on the filter is solubilized in 5 mL of ISTD solution (25.0 mg/L tetradecane in anhydrous alcohol), and heated at 60° C. for 30 minutes. The cooled solution is filtered through 0.45 μm pore size PTFE syringe filter and analyzed via GC-MS/FID. Three known perfume oils are used as comparison reference standards. Data Analysis involves summing the total area counts minus the ISTD area counts, and calculating an average Response Factor (RF) for the 3 standard perfumes. Then the Response Factor and total area counts for the product encapsulated perfumes are used along with the weight of the sample, to determine the total weight percent for each PRM in the encapsulated perfume. PRMs are identified from the mass spectrometry peaks.

(7) Volume Weighted Mean Particle Size

Particle size is measured using static light scattering devices, such as an Accusizer 780A, made by Particle Sizing Systems, Santa Barbara CA. The instrument is calibrated from 0 to 300μ using Duke particle size standards. Samples for particle size evaluation are prepared by diluting about 1 g emulsion, if the volume weighted mean particle size of the emulsion is to be determined, or 1 g of benefit agent containing delivery particles slurry, if the finished particles volume weighted mean particle size is to be determined, in about 5 g of de-ionized water and further diluting about 1 g of this solution in about 25 g of water.

About 1 g of the most dilute sample is added to the Accusizer and the testing initiated, using the autodilution feature. The Accusizer should be reading in excess of 9200 counts/second. If the counts are less than 9200 additional sample should be added. The accusizer will dilute the test sample until 9200 counts/second and initiate the evaluation. After 2 minutes of testing the Accusizer will display the results, including volume-weighted median size. The broadness index can be calculated by determining the particle size at which 95% of the cumulative particle volume is exceeded (95% size), the particle size at which 5% of the cumulative particle volume is exceeded (5% size), and the median volume-weighted particle size (50% size–50% of the particle volume both above and below this size). Broadness Index (5)=((95% size)–(5% size)/50% size).

(8) Polyvinyl Alcohol in Said Continuous Phase Based on Total Continuous Phase Water Weight and Polyvinyl Alcohol in Said Benefit Agent Containing Delivery Particle Based on Benefit Agent Containing Delivery Particle Core Weight Free polyvinyl alcohol level is determined using Capillary Gel Permeation Chromatography-Quadrupole Time-Of-Flight Mass Spectrometry The method is based on measuring the ion intensity of specific fragment ions generated in electrospray quadrupole time-of-flight mass spectrometer operated at an elevated collision energy (CE). Specifically the polyvinyl alcohol polymer molecule can be fragmented at CE 70V to generate unique marker ions, e.g., m/z 131. The ion intensity correlates with the polyvinyl alcohol concentration in the PMC slurry sample solutions.

Experimental Conditions

Calibration Solution Preparation 5% polyvinyl alcohol stock solution is first diluted to give 0.05% solution with de-ionized water (Millipore), then further a 2-fold serial dilution to cover the concentration range, 0.00078%-0.05%.

Sample Solution Preparation Each benefit agent containing delivery particles slurry solution is first diluted with water by 5 or 10 times, then filtered by passing them through 0.45 um PVDF membrane filters (PALL Gelman Lab).

Capillary Gel Permeation Chromatography-Mass Spectrometric Analysis ("GPC") Both calibration standard solutions and sample solutions are analyzed by injecting 5 ul onto a GPC system coupled to electrospray quadrupole time-of-flight mass spectrometer (QTOF, Waters, Beverly, MA) with four 1 mm i.d.×150 mm TSKGel G5000 or G6000 columns in series (Tosoh Bioscience, Japan), isocratic flow at 25 ul/min and a 30 min run time. The GPC buffer used is 5 mM ammonium acetate containing 10% acetonitrile. For mass spectrometric analysis, the first quadruple is operated at the wide band RF only mode so all ions are passed through the quadrupole, fragmented at CE 70V in the $2^{nd}$ quadrupole, and analyzed by the TOF mass analyzer. The mass range scanned is 50 to 3000 Da.

Data acquisition, processing and analysis The QTOF mass spectrometer uses MassLynx (Waters) for data acquisition and data processing. The peak intensity of the major polyvinyl alcohol fragment ion m/z 131 is measured and averaged from the two replicate CapGPC-QTOF runs. The polyvinyl alcohol percent concentration in each sample is calculated against the polyvinyl alcohol standard calibration curve. A good linearity covering is obtained under the current measurement conditions.

Bound polyvinyl alcohol level is calculated by using the following equation:

% bound polyvinyl alcohol=% total polyvinyl alcohol added to slurry−% free polyvinyl alcohol (9) Determination of Hydrolysis Degree of Polyvinyl Alcohol The hydrolysis degree, defined as percent hydrolysis means mole % hydrolysis of polyvinyl alcohol determined as follows. This measurement is a measure of the number of acetate groups that are replaced by hydroxyl groups during alcoholysis.

Degree of hydrolysis of polyvinyl alcohol is determined using the method of refluxing in strong base to hydrolyze remaining acetate groups and then back titrating with hydrochloric acid in accordance with the general principles outlined in established methods such as in the USP monograph for polyvinyl alcohol (USP39-NF34, pp. 5448-5449). One of skill in the art knows to choose sample size, vessel volumes, and the volume and concentration of reagents appropriately for the range of degree of hydrolysis being measured.

(10) Determination of Viscosity of Polyvinyl Alcohol

Viscosity is measured using a Brookfield LV series viscometer or equivalent, measured at 4.00%+/−0.05% solids.

a. Prepare a 4.00%+/−0.05% solid solution of polyvinyl alcohol.

Weigh a 500 mL beaker and stirrer. Record the weight. Add 16.00+/−0.01 grams of a polyvinyl alcohol sample to the beaker. Add approximately 350-375 mL of deionized water to the beaker and stir the solution. Place the beaker into a hot water bath with the cover plate. Agitate at moderate speed for 45 minutes to 1 hour, or until the polyvinyl alcohol is completely dissolved. Turn off the stirrer. Cool the beaker to approximately 20° C.

Calculate the final weight of the beaker as follows:

Final weight=(weight of empty beaker & stirrer)+(% solids as decimal×400)

Example: weight of empty beaker & stirrer=125.0 grams

% solids of polyvinyl alcohol (of the sample)=97.50% or 0.9750 as decimal

Final weight=125.0+(0.9750×400)=515.0 grams

Zero the top loading balance and place the beaker of polyvinyl alcohol solution with a propeller on it. Add deionized water to bring the weight up to the calculated final weight of 515.0 grams.

Solids content of the sample has to be 4.00+0.05% to measure viscosity.

b. Measure viscosity

Dispense the sample of 4% polyvinyl alcohol solution into the chamber of the viscometer, insert the spindle and attach it to the viscometer. Sample adapter (SSA) with chamber SC4-13RPY, Ultralow adapter. The spindles are SC4-18 and 00. Allow the sample to achieve equilibration at 20° C. temperature. Start the viscometer and record the steady state viscosity value.

Report viscosity <13 cP to nearest 0.01 cP, 13-100 cP to nearest 0.1 cP; viscosities over 100 cP are reported to the nearest 1 cP.

Corrections to the measured viscosity are not necessary if the calculated solution solids content is 4.00±0.05%. Otherwise, use the following equation to correct the measured viscosity for solution solids deviations.

$$\text{Log}_e \text{ Corrected Viscosity} = \frac{(\text{Log}_e \text{ Measured Viscosity})}{(\text{percent solids}) \times (0.2060) + (0.1759)}$$

Corrected Viscosity = 2.718282 (Log Corrected Viscosity)

(11) Number Average Molecular Weight of Polyvinyl Alcohol

A weight % of polyvinyl alcohol in water solution is prepared and the sample is injected into a GPC instrument:

Malvern Viscotek GPCmax VE 2001 sample module connected to a Malvern Viscotek

Model 305 TDA (Triple Detector Array)

Instrument Settings during analysis:

Solvent: water

Column Set: SOLDEX SB804+802.5

Flow rate: 0.750 mL/min

Injection Volume: 100 µl

Detector Temp: 30° C.

The result is reported in Daltons (Da).

(12) Degree of Polymerization of Polyvinyl Alcohol

Degree of polymerization is determined from the molecular weight data of the Number Average Molecular Weight test. Using the output from the GPC instrument, Degree of Polymerization is calculated from GPC value for $M_n$ $$\text{Degree of Polymerization} = \frac{Mn}{(86 - 0.42 \times \text{Degree of hydrolysis})}$$

EXAMPLES

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

Example 1

A first oil phase, consisting of 37.5 g perfume oil comprising:

a) from about 3% to about 20% of a perfume raw material selected from the group of Table 1 perfume raw materials 85-88, 100, 108 and mixtures thereof;
b) from about 2% to about 35% of a perfume raw material selected from the group of Table 1 perfume raw materials 62-84, 114, 115 and mixtures thereof;
c) from about 2% to about 35% of a perfume raw material selected from the group of Table 1 perfume raw materials 1-61, 101, 102, 104, 109, 113 and mixtures thereof;
d) from about 0% to about 10% of a perfume raw material selected from the group of Table 1 perfume raw materials 99, 106, 111, 112 and mixtures thereof;
e) from about 0% to about 10% of a perfume raw material selected from the group of Table 1 perfume raw materials 89-94, 107, 110 and mixtures thereof; and
f) from about 0% to about 0.5% of a perfume raw material selected from the group of Table 1 perfume raw materials 95-98, 103, 105 and mixtures thereof. 0.2 g tert-butylamino ethyl methoacrylate, and 0.2 g beta hydroxyethyl acrylate is mixed for about 1 hour before the addition of 18 g CN975 (Sartomer, Exter, PA). The solution is allowed to mix until needed later in the process.

A second oil phase consisting of 65 g of the perfume oil, 84 g isopropyl myristate, 1 g 2,2'-azobis(2-methylbutyronitrile), and 0.8 g 4,4'-azobis[4-cyanovaleric acid] is added to a jacketed steel reactor. The reactor is held at 35° C. and the oil solution in mixed at 500 rpm's with a 2" flat blade mixer. A nitrogen blanket is applied to the reactor at a rate of 300 cc/min. The solution is heated to 70° C. in 45 minutes and held at 70° C. for 45 minutes, before cooling to 50° C. in 75 minutes. At 50° C., the first oil phase is added and the combined oils are mixed for another 10 minutes at 50° C.

A water phase, containing 85 g Celvol 540 polyvinyl alcohol (Sekisui Specialty Chemicals, Dallas, TX) at 5% solids, 268 g water, 1.2 g 4,4'-azobis[4-cyanovaleric acid], and 1.1 g 21.5% NaOH, is prepared and mixed until the 4,4'-AZOBIS[4-CYANOVALERIC ACID] dissolves. The water phase pH for this batch was 4.90.

Once the oil phase temperature has decreased to 50° C., mixing is stopped and the water phase is added to the mixed oils. High shear agitation is applied to produce an emulsion with the desired size characteristics (1900 rpm's for 60 minutes.) The temperature was increased to 75° C. in 30 minutes, held at 75° C. for 4 hours, increased to 95° C. in 30 minutes, and held at 95° C. for 6 hours. The batch was allowed to cool to room temperature. The benefit agent containing delivery particles had a volume-weighted median size of 20 microns.

From a total of 1.2% polyvinyl alcohol added to the batch, the level of free polyvinyl alcohol measured in the water phase was 0.44%.

Example 2

Example 2 was similarly prepared as Example 1, except the amount of water in the water phase was increased to 340 grams. The water phase pH was 4.84. After the batch was completed, the batch was reheated to 85° C. and mixed to allow 72 grams of water to evaporate off from the batch. Volume-weighted median size of the benefit agent containing delivery particles was 19.8 microns.

From a total of 1.2% polyvinyl alcohol added to the batch, the level of free polyvinyl alcohol measured in the water phase was 0.44%.

Example 3

Example 3 was similarly prepared as Example 1, except the amount of water in the water phase was decreased to 188 grams. The water phase pH was 4.84. After the batch was completed, 80 grams of water was added back into the batch. Volume-weighted median size of the benefit agent containing delivery particles was 19.8 microns.

From a total of 1.2% polyvinyl alcohol added to the batch, the level of free polyvinyl alcohol measured in the water phase was 0.47%.

Example 4

Example 4 was similarly prepared as Example 1, except the amount of Celvol 540 polyvinyl alcohol was increased to 127 grams. The water phase pH was 4.84. Volume-weighted median size of the benefit agent containing delivery particles was 19.8 microns.

From a total of 1.6% polyvinyl alcohol added to the batch, the level of free polyvinyl alcohol measured in the water phase was 0.87%.

Example 5

Example 5 was similarly prepared as Example 1, except the amount of Celvol 540 polyvinyl alcohol was decreased to 56 grams. The water phase pH was 4.84. Volume-weighted median size of the benefit agent containing delivery particles was 19.8 microns.

From a total of 0.86% polyvinyl alcohol added to the batch, the level of free polyvinyl alcohol measured in the water phase was 0.26%.

Example 6

A first oil phase, consisting of 200 g perfume oil, 1.2 g tert-butylamino ethyl methoacrylate, and 1.2 g beta hydroxyethyl acrylate is mixed for about 1 hour before the addition of 99 g CN975 (Sartomer, Exter, PA). The solution is allowed to mix until needed later in the process. A second oil phase consisting of 360 g of the perfume oil, 460 g isopropyl myristate, 5.5 g 2,2'-azobis(2-methylbutyronitrile), and 4.4 g 4,4'-azobis[4-cyanovaleric acid] is added to a jacketed steel reactor. The reactor is held at 35° C. and the oil solution in mixed at 500 rpm's with a 2" flat blade mixer. A nitrogen blanket is applied to the reactor at a rate of 300 cc/min. The solution is heated to 70° C. in 45 minutes and held at 70° C. for 45 minutes, before cooling to 50° C. in 75 minutes. At 50° C., the first oil phase is added and the combined oils are mixed for another 10 minutes at 50° C.

A water phase, containing 233 g Celvol 540 polyvinyl alcohol (Sekisui Specialty Chemicals, Dallas, TX) at 5% solids, 1224 g water, 6.6 g 4,4'-azobis[4-cyanovaleric acid], and 6 g 21.5% NaOH, is prepared and mixed until the 4,4'-AZOBIS[4-CYANOVALERIC ACID] dissolves. The water phase pH for this batch was 4.90.

Once the oil phase temperature has decreased to 50° C., mixing is stopped and the water phase is added to the mixed oils. High shear agitation is applied to produce an emulsion with the desired size characteristics (3100 rpm's for 60 minutes.)

The temperature was increased to 75° C. in 30 minutes, held at 75° C. for 4 hours, increased to 95° C. in 30 minutes, and held at 95° C. for 6 hours. The batch was allowed to cool to room temperature. The benefit agent containing delivery particles had a volume-weighted median size of 18 microns and 0.8% total polyvinyl alcohol, was added to the batch.

Example 7

Example 7 was similarly prepared as Example 6, except the amount of Celvol 540 polyvinyl alcohol (Sekisui Specialty Chemicals, Dallas, TX) was increased to 350 g and the amount of water was decreased to 1100 g. The water phase pH was 4.8. Volume-weighted median size of the benefit agent containing delivery particles was 18 microns and 1.2% total polyvinyl alcohol, was added to the batch.

Example 8

Example 8 was similarly prepared as Example 6, except the amount of Celvol 540 polyvinyl alcohol (Sekisui Specialty Chemicals, Dallas, TX) was increased to 525 g and the amount of water was decreased to 933 g. The water phase pH was 4.8. Volume-weighted median size of the benefit agent containing delivery particles was 19 microns and 1.8% total polyvinyl alcohol, was added to the batch.

The benefit agent containing delivery particle slurries described in Examples 6 through 8 were refined with water & centrifuging to remove some of the unbound ("free") polyvinyl alcohol. Slurries were diluted with water to 28-30% solids and heated to 70° C. Each batch was fed through a continuous centrifuge with a bowl speed of 50 Hz (~9000 rpm) and a target split ratio of 60% lights (accepts stream) and 40% heavies (rejects stream). The lights stream was collected and the heavies stream was discarded. The dilution, heating, and centrifugation procedure was repeated a second time using the half of the lights collected from each batch.

Slurries from Examples 6 through 8 were analyzed for free and bound polyvinyl alcohol level for unrefined, once refined, & twice refined samples. Results are summarized in the table below

| Example | Refining | % Added Polyvinyl alcohol | % Free Polyvinyl alcohol | % Bound Polyvinyl alcohol |
|---|---|---|---|---|
| 6 | None | 0.8 | 0.38 | 0.42 |
| | 1x | | 0.17 | |
| | 2x | | 0.09 | |
| 7 | None | 1.2 | 0.62 | 0.58 |
| | 1x | | 0.26 | |
| | 2x | | 0.12 | |
| 8 | None | 1.8 | 0.92 | 0.88 |
| | 1x | | 0.41 | |
| | 2x | | 0.18 | |

Example 9

Unrefined slurry samples with 0.8%, 1.2%, & 1.8% total polyvinyl alcohol were prepared in a similar manner as Examples 6-8. Magnesium chloride & xanthan gum (Novaxxan—ADM) were mixed into the slurries at room temperature to structure the solids & placed into storage at 30° C. & 40° C. in 4 oz glass containers. Phase separation was measured after one month.

| % Total Polyvinyl alcohol | % Xanthan gum | % MgCl2 | % Separation @30 C. | % Separation @40 C. |
|---|---|---|---|---|
| 0.8 | 0.16 | 0 | 0.0 | 0.0 |
| | 0.28 | 0.6 | 2.50 | 2.78 |
| | 0.16 | 0.6 | 5.26 | 7.89 |
| | 0.16 | 1 | 5.0 | 10.26 |
| | 0.28 | 1 | 5.41 | 5.71 |
| 1.2 | 0.28 | 0 | 0.0 | 0.0 |
| | 0.28 | 0.6 | 21.95 | 26.25 |
| | 0.36 | 0 | 0.0 | 3.85 |
| | 0.36 | 0.6 | 23.08 | 23.68 |
| 1.8 | 0.28 | 0 | 20.97 | 22.5 |
| | 0.28 | 0.6 | 28.95 | 30.0 |
| | 0.36 | 0 | 13.89 | 17.50 |
| | 0.36 | 0.6 | 27.78 | 25.0 |

Example 10

An unrefined slurry sample with 1.2% total polyvinyl alcohol, along with unrefined & refined samples with 1.8% total polyvinyl alcohol, were prepared in a similar manner as Examples 6 & 8 and placed into storage at 30° C. & 40° C. in 4 oz glass containers. Phase separation was measured after one month.

| % Total Polyvinyl alcohol | % Xanthan gum | % MgCl2 | % Separation @30 C. | % Separation @40 C. |
|---|---|---|---|---|
| 0.8 | 0.2 | 0 | 0.0 | 0.0 |
| 1.8 | 0.2 | 0 | 15.2 | 22.5 |
| 1.8* | 0.12 | 0 | 0.0 | 1.7 |

*1x refined sample

Non-limiting examples of product formulations containing Benefit agent containing delivery particles disclosed in the present specification are summarized in the following tables.

Example 11

Solid free-flowing particulate laundry detergent composition examples

| Ingredient | Amount (in wt %) |
|---|---|
| Anionic detersive surfactant (such as alkyl benzene sulphonate, alkyl ethoxylated sulphate and mixtures thereof) | from 8 wt % to 15 wt % |
| Non-ionic detersive surfactant (such as alkyl ethoxylated alcohol) | from 0.1 wt % to 4 wt % |
| Cationic detersive surfactant (such as quaternary ammonium compounds) | from 0 wt % to 4 wt % |
| Other detersive surfactant (such as zwitterionic detersive surfactants, amphoteric surfactants and mixtures thereof) | from 0 wt % to 4 wt % |
| Carboxylate polymer (such as co-polymers of maleic acid and acrylic acid and/or carboxylate | from 0.1 wt % to 4 wt % |

-continued

| Ingredient | Amount (in wt %) |
|---|---|
| polymers comprising ether moieties and sulfonate moieties) | |
| Polyethylene glycol polymer (such as a polyethylene glycol polymer comprising polyvinyl acetate side chains) | from 0 wt % to 4 wt % |
| Polyester soil release polymer (such as Repel-o-tex and/or Texcare polymers) | from 0 wt % to 2 wt % |
| Cellulosic polymer (such as carboxymethyl cellulose, methyl cellulose and combinations thereof) | from 0.5 wt % to 2 wt % |
| Other polymer (such as care polymers) | from 0 wt % to 4 wt % |
| Zeolite builder and phosphate builder (such as zeolite 4A and/or sodium tripolyphosphate) | from 0 wt % to 4 wt % |
| Other co-builder (such as sodium citrate and/or citric acid) | from 0 wt % to 3 wt % |
| Carbonate salt (such as sodium carbonate and/or sodium bicarbonate) | from 0 wt % to 20 wt % |
| Silicate salt (such as sodium silicate) | from 0 wt % to 10 wt % |
| Filler (such as sodium sulphate and/or bio-fillers) | from 10 wt % to 70 wt % |
| Source of hydrogen peroxide (such as sodium percarbonate) | from 0 wt % to 20 wt % |
| Bleach activator (such as tetraacetylethylene diamine (TAED) and/or nonanoyloxybenzenesulphonate (NOBS)) | from 0 wt % to 8 wt % |
| Bleach catalyst (such as oxaziridinium-based bleach catalyst and/or transition metal bleach catalyst) | from 0 wt % to 0.1 wt % |
| Other bleach (such as reducing bleach and/or pre-formed peracid) | from 0 wt % to 10 wt % |
| Photobleach (such as zinc and/or aluminum sulphonated phthalocyanine) | from 0 wt % to 0.1 wt % |
| Chelant (such as ethylenediamine-N'N'-disuccinic acid (EDDS) | from 0.2 wt % to 1 wt % |

-continued

| Ingredient | Amount (in wt %) |
|---|---|
| and/or hydroxyethane diphosphonic acid (HEDP)) | |
| Hueing agent (such as direct violet 9, 66, 99, acid red 50, solvent violet 13 and any combination thereof) | from 0 wt % to 1 wt % |
| Protease (such as Savinase, Savinase Ultra, Purafect, FN3, FN4 and any combination thereof) | from 0.1 wt % to 0.4 wt % |
| Amylase (such as Termamyl, Termamyl ultra, Natalase, Optisize, Stainzyme, Stainzyme Plus and any combination thereof) | from 0 wt % to 0.2 wt % |
| Cellulase (such as Carezyme and/or Celluclean) | from 0 wt % to 0.2 wt % |
| Lipase (such as Lipex, Lipolex, Lipoclean and any combination thereof) | from 0 wt % to 1 wt % |
| Other enzyme (such as xyloglucanase, cutinase, pectate lyase, mannanase, bleaching enzyme) | from 0 wt % to 2 wt % |
| Fabric softener (such as montmorillonite clay and/or polydimethylsiloxane (PDMS)) | from 0 wt % to 15 wt % |
| Flocculant (such as polyethylene oxide) | from 0 wt % to 1 wt % |
| Suds suppressor (such as silicone and/or fatty acid) | from 0 wt % to 4 wt % |
| Benefit agent containing delivery particles according to the invention including Examples 1-8 and mixtures thereof | from 0.1 wt % to 1 wt % |
| Perfume (such as spray-on perfume, starch encapsulated perfume accords, perfume loaded zeolite, and any combination thereof) | from 0.1 wt % to 1 wt % |
| Aesthetics (such as coloured soap rings and/or coloured speckles/noodles) | from 0 wt % to 1 wt % |
| Miscellaneous | balance to 100 wt % |

Examples 12 Heavy Duty Liquid Laundry Detergent Compositions

| | A (wt %) | B (wt %) | C (wt %) | D (wt %) | E (wt %) | F (wt %) | G (wt %) |
|---|---|---|---|---|---|---|---|
| AES $C_{12-15}$ alkyl ethoxy (1.8) sulfate | 11 | 10 | 4 | 6.32 | 0 | 0 | 0 |
| AE3S | 0 | 0 | 0 | 0 | 2.4 | 0 | 0 |
| Linear alkyl benzene sulfonate/sulfonic acid | 1.4 | 4 | 8 | 3.3 | 5 | 8 | 19 |
| HSAS | 3 | 5.1 | 3 | 0 | 0 | 0 | 0 |
| Sodium formate | 1.6 | 0.09 | 1.2 | 0.04 | 1.6 | 1.2 | 0.2 |
| Sodium hydroxide | 2.3 | 3.8 | 1.7 | 1.9 | 1.7 | 2.5 | 2.3 |
| Monoethanolamine | 1.4 | 1.49 | 1.0 | 0.7 | 0 | 0 | To pH 8.2 |
| Diethylene glycol | 5.5 | 0.0 | 4.1 | 0.0 | 0 | 0 | 0 |
| AE9 | 0.4 | 0.6 | 0.3 | 0.3 | 0 | 0 | 0 |
| AE8 | 0 | 0 | 0 | 0 | 0 | 0 | 20.0 |
| AE7 | 0 | 0 | 0 | 0 | 2.4 | 6 | 0 |
| Chelant (HEDP) | 0.15 | 0.15 | 0.11 | 0.07 | 0.5 | 0.11 | 0.8 |
| Citric Acid | 2.5 | 3.96 | 1.88 | 1.98 | 0.9 | 2.5 | 0.6 |
| $C_{12-14}$ dimethyl Amine Oxide | 0.3 | 0.73 | 0.23 | 0.37 | 0 | 0 | 0 |
| $C_{12-18}$ Fatty Acid | 0.8 | 1.9 | 0.6 | 0.99 | 1.2 | 0 | 15.0 |
| 4-formyl-phenylboronic acid | 0 | 0 | 0 | 0 | 0.05 | 0.02 | 0.01 |
| Borax | 1.43 | 1.5 | 1.1 | 0.75 | 0 | 1.07 | 0 |
| Ethanol | 1.54 | 1.77 | 1.15 | 0.89 | 0 | 3 | 7 |
| A compound having the following general structure: bis$((C_2H_5O)(C_2H_4O)n)(CH_3)$—$N^+$—$C_xH_{2x}$—$N^+$—$(CH_3)$-bis$((C_2H_5O)(C_2H_4O)n)$, wherein n = from 20 to 30, and x = from 3 to 8, or sulphated or sulphonated variants thereof | 0.1 | 0 | 0 | 0 | 0 | 0 | 2.0 |
| Ethoxylated ($EO_{15}$) tetraethylene pentamine | 0.3 | 0.33 | 0.23 | 0.17 | 0.0 | 0.0 | 0 |
| Ethoxylated Polyethylenimine | 0 | 0 | 0 | 0 | 0 | 0 | 0.8 |
| Ethoxylated hexamethylene diamine | 0.8 | 0.81 | 0.6 | 0.4 | 1 | 1 | |
| 1,2-Propanediol | 0.0 | 6.6 | 0.0 | 3.3 | 0.5 | 2 | 8.0 |

-continued

| | A (wt %) | B (wt %) | C (wt %) | D (wt %) | E (wt %) | F (wt %) | G (wt %) |
|---|---|---|---|---|---|---|---|
| Hydrogenated castor oil derivative structurant | 0.1 | 0 | 0 | 0 | 0 | 0 | 0.1 |
| Perfume | 1.6 | 1.1 | 1.0 | 0.8 | 0.9 | 1.5 | 1.6 |
| Protease (40.6 mg active/g) | 0.8 | 0.6 | 0.7 | 0.9 | 0.7 | 0.6 | 1.5 |
| Mannanase: Mannaway ® (25 mg active/g) | 0.07 | 0.05 | 0.045 | 0.06 | 0.04 | 0.045 | 0.1 |
| Amylase: Stainzyme ® (15 mg active/g) | 0.3 | 0 | 0.3 | 0.1 | 0 | 0.4 | 0.1 |
| Amylase: Natalase ® (29 mg active/g) | 0 | 0.2 | 0.1 | 0.15 | 0.07 | 0 | 0.1 |
| Xyloglucanase (Whitezyme ®, 20 mg active/g) | 0.2 | 0.1 | 0 | 0 | 0.05 | 0.05 | 0.2 |
| Lipex ® (18 mg active/g) | 0.4 | 0.2 | 0.3 | 0.1 | 0.2 | 0 | 0 |
| Neat Perfume (1) | 0.5 | 0.5 | 0.5 | 0.5 | 0.5 | 0.5 | 0.5 |
| Perfume containing delivery particles (2) | 0.25 | 3.2 | 2.5 | 4.0 | 2.5 | 1.4 | 0.8 |
| *Water, dyes & minors | | | | Balance | | | |

*Based on total cleaning and/or treatment composition weight, a total of no more than 12% water (1) Optional.

(2) Benefit agent containing delivery particles of the present invention comprising a core that comprises perfume and/or a silicone including Examples 1-8 and mixtures thereof.

Examples, 13 Unit Dose Compositions

| Example of Unit Dose detergents | A | B | C | D |
|---|---|---|---|---|
| alkyl polyethoxylate nonionic surfactant | 5 | 15 | 25 | 25 |
| Alkyl ethoxy sulfate | 15 | 10 | — | |
| Linear Alkylbenzene sulfonic acid | 20 | 15 | 25 | 15 |
| Citric Acid | 1 | 0.5 | — | 3 |
| Fatty Acid | 5 | 10 | 10 | 15 |
| Enzymes | 1 | 1.5 | 1 | 0.5 |
| Chelant | 2 | 2 | 0.5 | 1 |
| Hydrogenated Castor Oil | 0.2 | 0.2 | — | — |
| Organic solvent (propanediol, glycerol, dipropyleneglycol, ethanol) | 25 | 25 | 15 | 25 |
| Mono Ethanol Amine | 10 | 6 | 8 | 7 |
| Perfume containing delivery particles (2) | 0.9 | 0.9 | 1.5 | 1.5 |

-continued

| Example of Unit Dose detergents | A | B | C | D |
|---|---|---|---|---|
| Water and minors (neat perfume, dye, preservatives, . . . ) | Up to 100% | Up to 100% | Up to 100% | Up to 100% |

(2) Benefit agent containing delivery particles according to present invention comprising a core that comprises perfume including Examples 1-8 and mixtures thereof Example 14

Examples of free flowing particles products that comprise benefit agent containing delivery particles according to the present invention. The table below also exemplifies combinations which comprise also perfume free and in benefit agent containing delivery particles or combinations of these with aforementioned combinations with malodor reduction materials and/or compositions.

| | COMPOSITION | | | |
|---|---|---|---|---|
| Component | 1 % Wt Active | 2 % Wt Active | 3 % Wt Active | 4 % Wt Active |
| Polyethylene glycol | 70-99 | 0-20 | 0-29 | 0-40 |
| Clay | 0-29 | 0-20 | 0-20 | 0-10 |
| NaCl | 0-29 | 50-99 | 0-29 | 0-40 |
| Na2SO4 | 0-10 | 0-10 | 0-10 | 0-5 |
| Urea | 0-29 | 0-29 | 0-99 | 0-40 |
| Zeolite | 0-29 | 0-29 | 0-29 | 0-5 |
| Plasticizers/Solvents | | | | |
| Starch/Zeolite | 0-29 | 0-29 | 0-29 | 0-5 |
| Silica | 0-5 | 0-5 | 0-5 | 0-5 |
| Metal oxide | 0-29 | 0-29 | 0-29 | 0-29 |
| Metal catalyst | 0.001-0.5 | 0.001-0.5 | 0.001-0.5 | 0.001-0.5 |
| Opacifier | 0-5 | 0-5 | 0-1 | 0-1 |
| Water | 0-2 | 0-2 | 0-5 | 0-5 |
| Perfume | 0-5 | 0-5 | 0-5 | 0-5 |
| Benefit agent containing delivery particles according to the present invention including Examples 1-8 and mixtures thereof | 0.001-10 | 0.001-4.5 | 0.001-3 | 0.001-7.5 |

-continued

| Component | COMPOSITION 5 % Wt Active | 6 % Wt Active | 7 % Wt Active | 8 % Wt Active |
|---|---|---|---|---|
| Polyethylene glycol | 70-99 | 0-20 | 0-29 | 0-40 |
| Clay | 0-29 | 0-20 | 0-20 | 0-10 |
| NaCl | 0-29 | 50-99 | 0-29 | 0-40 |
| Na2SO4 | 0-10 | 0-10 | 0-10 | 0-5 |
| Urea | 0-29 | 0-29 | 0-99 | 0-40 |
| Zeolite | 0-29 | 0-29 | 0-29 | 0-5 |
| Plasticizers/Solvents | | | | |
| Starch/Zeolite | 0-29 | 0-29 | 0-29 | 0-5 |
| Silica | 0-5 | 0-5 | 0-5 | 0-5 |
| Metal oxide | 0-29 | 0-29 | 0-29 | 0-29 |
| Metal catalyst | 0.001-0.5 | 0.001-0.5 | 0.001-0.5 | 0.001-0.5 |
| Opacifier | 0-5 | 0-5 | 0-1 | 0-1 |
| Water | 0-2 | 0-2 | 0-5 | 0-5 |
| Benefit agent containing delivery particles according to the present invention including Examples 1-8 and mixtures thereof | 0.001-10 | 0.001-4.5 | 0.001-3 | 0.001-7.5 |

Example 15

Examples of liquid fabric softening products that comprise benefit agent containing delivery particles according to the present invention. The table below also exemplifies combinations which comprise also perfume free and in benefit agent containing delivery particles or combinations of these with aforementioned combinations with malodor reduction materials and/or compositions.

| | A |
|---|---|
| Deionized water | balance |
| Chelant | 0.005-0.05 |
| Preservative | 0.01-0.04 |
| Quaternary ammonium ester softening active | 4-20 |
| Antifoam | 0.05-0.2 |
| Perfume containing delivery particles according to the invention including Examples 1-8 and mixtures thereof | 0.2-1.5 |
| Dye | 0.005-0.02 |
| Polymeric thickener | 0.05-0.5 |
| Free Perfume | 2.0 |

Raw Materials and Notes for Composition Examples

LAS is linear alkylbenzenesulfonate having an average aliphatic carbon chain length $C_9$-$C_{15}$ supplied by Stepan, Northfield, Illinois, USA or Huntsman Corp. (HLAS is acid form).

$C_{12-14}$ Dimethylhydroxyethyl ammonium chloride, supplied by Clariant GmbH, Germany AE3S is $C_{12-15}$ alkyl ethoxy (3) sulfate supplied by Stepan, Northfield, Illinois, USA AE7 is $C_{12-15}$ alcohol ethoxylate, with an average degree of ethoxylation of 7, supplied by Huntsman, Salt Lake City, Utah, USA AES is $C_{10-18}$ alkyl ethoxy sulfate supplied by Shell Chemicals.

AE9 is $C_{12-13}$ alcohol ethoxylate, with an average degree of ethoxylation of 9, supplied by Huntsman, Salt Lake City, Utah, USA HSAS or HC1617HSAS is a mid-branched primary alkyl sulfate with average carbon chain length of about 16-17

Sodium tripolyphosphate is supplied by Rhodia, Paris, France

Zeolite A is supplied by Industrial Zeolite (UK) Ltd, Grays, Essex, UK 1.6 R Silicate is supplied by Koma, Nestemica, Czech Republic Sodium Carbonate is supplied by Solvay, Houston, Texas, USA Polyacrylate MW 4500 is supplied by BASF, Ludwigshafen, Germany Carboxymethyl cellulose is Finnfix® V supplied by CP Kelco, Arnhem, Netherlands Suitable chelants are, for example, diethylenetetraamine pentaacetic acid (DTPA) supplied by Dow Chemical, Midland, Michigan, USA or Hydroxyethane di phosphonate (HEDP) supplied by Solutia, St Louis, Missouri, USA Bagsvaerd, Denmark Savinase®, Natalase®, Stainzyme®, Lipex®, Celluclean™, Mannaway® and Whitezyme® are all products of Novozymes, Bagsvaerd, Denmark.

Proteases may be supplied by Genencor International, Palo Alto, California, USA (e.g. Purafect Prime®) or by Novozymes, Bagsvaerd, Denmark (e.g. Liquanase®, Coronase®).

Sodium percarbonate supplied by Solvay, Houston, Texas, USA

Sodium perborate is supplied by Degussa, Hanau, Germany

NOBS is sodium nonanoyloxybenzenesulfonate, supplied by Future Fuels, Batesville, USA TAED is tetraacetylethylenediamine, supplied under the Peractive® brand name by Clariant GmbH, Sulzbach, Germany S-ACMC is carboxymethylcellulose conjugated with C.I. Reactive Blue 19, sold by Megazyme, Wicklow, Ireland under the product name AZO-CM-CELLULOSE, product code S-ACMC.

Soil release agent is Repel-o-Tex® PF, supplied by Rhodia, Paris, France

Acrylic Acid/Maleic Acid Copolymer is molecular weight 70,000 and acrylate:maleate ratio 70:30, supplied by BASF, Ludwigshafen, Germany Na salt of Ethylenediamine-N,N'-disuccinic acid, (S,S) isomer (EDDS) is supplied by Octel, Ellesmere Port, UK Hydroxyethane di phosphonate (HEDP) is supplied by Dow Chemical, Midland, Michigan, USA Suds suppressor agglomerate is supplied by Dow Corning, Midland, Michigan, USA HSAS is mid-branched alkyl sulfate as disclosed in U.S. Pat. Nos. 6,020,303 and 6,060,443

$C_{12-14}$ dimethyl Amine Oxide is supplied by Procter & Gamble Chemicals, Cincinnati, USA Random graft copolymer is a polyvinyl acetate grafted polyethylene oxide copolymer having a polyethylene oxide backbone and multiple polyvinyl acetate side chains. The molecular weight of the polyethylene oxide backbone is about 6000 and the weight ratio of the polyethylene oxide to polyvinyl acetate is about 40:60 and no more than 1 grafting point per 50 ethylene oxide units.

Ethoxylated polyethyleneimine is polyethyleneimine (MW=600) with 20 ethoxylate groups per —NH.

Cationic cellulose polymer is LK400, LR400 and/or JR30M from Amerchol Corporation, Edgewater NJ Note: all enzyme levels are expressed as % enzyme raw material.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A composition comprising a consumer product adjunct material and benefit agent containing delivery particles comprising a core and a shell encapsulating said core, said benefit agent containing delivery particles comprising:

a) based on total benefit agent containing delivery particle core weight from 0.1% to 0.9% polyvinyl alcohol; said polyvinyl alcohol based on total encapsulated benefit agent particle core weight having at least one of the following properties:

(i) a hydrolysis degree from about 55% to about 99%;

(ii) a viscosity of from about 40 mPa·s to about 120 mPa·s in 4% water solution at 20° C.;

(iii) a degree of polymerization of from about 1,500 to about 2,500;

(iv) number average molecular weight of from about 65,000 Da to about 110,000 Da;

b) said benefit agent containing delivery particles having a volume weighted mean particle size from about 0.5 microns to about 100 microns, said benefit agent containing delivery particles' shell comprising, said polyvinyl alcohol and one or more polyacrylate polymers, said core comprising, based on total core weight, greater than 10% of a partitioning modifier that comprises a material selected from the group consisting of propan-2-yl tetradecanoate, vegetable oil, modified vegetable oil, and mixtures thereof;

said composition being a consumer product.

2. The composition of claim 1 wherein said partitioning modifier comprises propan-2-yl tetradecanoate.

3. The composition according to claim 1 wherein said shell comprises a polyacrylate.

4. The composition according to claim 1, wherein said shell comprises a polymer derived from a material that comprises one or more multifunctional acrylate moieties.

5. The composition according to claim 1, wherein said shell comprises a polymer derived from a material that comprises one or more multifunctional acrylate and/or methacrylate moieties.

6. The composition according to claim 1, wherein said benefit agent containing delivery particles having a volume weighted mean particle size from about 5 microns to about 45 microns or a volume weighted mean particle size from about 25 microns to about 60 microns, said composition comprising, based on total composition weight, from about 0.1% to about 35% of a fabric softener active.

7. The composition according to claim 1, said composition comprising, based on total composition weight, from about 5% to about 95% of a surfactant.

8. The composition according to claim 1 wherein said composition comprises, based on total composition weight, from about 5% to about 20% water, said composition being encased in a film.

9. The composition according to claim 1, said composition comprising a liquid and/or gel and a film, said film encasing said liquid and/or gel, optionally said liquid or gel comprising a suspended solid.

10. The composition according to claim 1, wherein said benefit agent containing delivery particles have a volume weighted mean particles size from about 2 microns to about 40 microns, said composition comprising based on total composition weight, from about 5% to about 95% free water and from about 0.5% to about 25% of a builder.

11. The composition according to claim 1, comprising, based on total composition weight, a material selected from the group consisting of a hueing dye, a structurant, a perfume delivery system and mixtures thereof.

12. The composition according to claim 1, wherein said benefit agent containing delivery particles are produced by a radical polymerization process that comprises the step of combining, based on total radical polymerization process acrylate monomer reactants, from about 50% to about 100% of a hexa-functional urethane acrylate and/or a penta-functional urethane acrylate, from about 0% to about 25% of a methacrylate that comprises an amino moiety and from about 0% to about 25% of an acrylate comprising a carboxyl moiety, with the proviso that the sum of the hexa-functional urethane acrylate and/or penta-functional urethane acrylate, methacrylate that comprises an amino moiety and acrylate comprising a carboxyl moiety, is 100%.

13. The composition according to claim 12, wherein said methacrylate that comprises an amino moiety comprises tertiarybutylaminoethyl methacrylate and said acrylate comprising a carboxyl moiety comprises beta carboxyethyl acrylate.

14. The composition according to claim 1, comprising a deposition aid.

15. The composition according to claim 14, wherein said deposition aid coats the outer surface of said delivery particles' shell.

16. The composition according to claim 14, wherein said deposition aid comprises a material selected from the group consisting of poly(meth)acrylate, poly(ethylene-maleic anhydride), polyamine, wax, polyvinylpyrrolidone, polyvinylpyrrolidone co-polymers, polyvinylpyrrolidone-ethyl acrylate, polyvinylpyrrolidone-vinyl acrylate, polyvinylpyrrolidone methylacrylate, polyvinylpyrrolidone/vinyl acetate, polyvinyl acetal, polyvinyl butyral, polysiloxane, poly(propylene maleic anhydride), maleic anhydride derivatives, co-polymers of maleic anhydride derivatives, polyvinyl alcohol, styrene-butadiene latex, gelatin, gum Arabic, carboxymethyl cellulose, carboxymethyl hydroxyethyl cellulose, hydroxyethyl cellulose, sodium alginate, chitosan, casein, pectin, modified starch, polyvinyl methyl ether/maleic anhydride, poly(vinyl pyrrolidone/methacrylamidopropyl trimethyl ammonium chloride), polyvinyl pyrrolidone/dimethylaminoethyl methacrylate, polyvinyl amines, polyvinyl formamides, polyallyl amines and copolymers of polyvinyl amines, and mixtures thereof.

17. The composition according to claim 14, wherein said deposition aid comprises a material selected from the group consisting of poly(meth)acrylates, poly(ethylene-maleic anhydride), polyamine, polyvinylpyrrolidone, polyvinylpyrrolidone-ethyl acrylate, polyvinylpyrrolidone-vinyl acrylate, polyvinylpyrrolidone methylacrylate, polyvinylpyrrolidone/vinyl acetate, polyvinyl acetal, polyvinyl butyral, polysiloxane, poly(propylene maleic anhydride), maleic anhydride derivatives, co-polymers of maleic anhydride derivatives, polyvinyl alcohol, chitosan, carboxymethyl cellulose, carboxymethyl hydroxyethyl cellulose, hydroxyethyl cellulose, polyvinyl methyl ether/maleic anhydride, poly(vinyl pyrrolidone/methacrylamidopropyl trimethyl ammonium chloride), polyvinyl pyrrolidone/dimethylaminoethyl methacrylate, polyvinyl amines, polyvinyl formamides, polyallyl amines and copolymers of polyvinyl amines, and mixtures thereof.

18. A method of treating and/or cleaning a situs, said method comprising a) optionally washing, rinsing and/or drying said situs;

b) contacting said situs with the composition according to claim 1; and c) optionally washing, rinsing and/or drying said situs wherein said drying steps comprise active drying and/or passive drying.

* * * * *